United States Patent [19]

Albarella et al.

[11] Patent Number: 5,130,433
[45] Date of Patent: Jul. 14, 1992

[54] CHROMOGENIC THIOL INDICATORS BASED ON AN ISOBENZOTHIAZOLONE RING SYSTEM

[75] Inventors: James P. Albarella; David L. Garling; Robert P. Hatch, all of Elkhart, Ind.

[73] Assignee: Miles Inc., Elkhart, Ind.

[21] Appl. No.: 546,703

[22] Filed: Jul. 2, 1990

Related U.S. Application Data

[63] Continuation of Ser. No. 214,426, Jul. 1, 1988, abandoned.

[51] Int. Cl.[5] .............................. C07D 275/04
[52] U.S. Cl. .................................. 546/159; 546/270; 548/181; 548/209
[58] Field of Search ............... 548/209, 181; 534/788, 534/780; 546/270, 159

[56] References Cited

U.S. PATENT DOCUMENTS

| | | | |
|---|---|---|---|
| 2,767,174 | 10/1956 | Katz et al. | 548/209 X |
| 3,812,138 | 3/1974 | Heise et al. | 534/788 X |
| 3,862,955 | 1/1975 | Grivas | 548/209 |
| 3,878,189 | 4/1975 | Coates et al. | 534/788 X |
| 3,975,155 | 8/1976 | Geyer | 548/209 X |
| 4,156,729 | 5/1979 | Boshagbn et al. | 548/209 X |
| 4,212,872 | 7/1980 | Baggaley | 548/209 X |
| 4,243,669 | 1/1981 | Baggaley | 548/209 X |
| 4,550,168 | 10/1985 | Welter et al. | 548/209 X |

OTHER PUBLICATIONS

Ponci et al I, Chemical Abstracts, vol. 60, No. 2912h (1964).
Ponci et al II, Chemical Abstracts, vol. 61, No. 3088h (1964).
Ponci et al III, Chemical Abstracts, vol. 61, No. 6299h (1964).

Primary Examiner—Mary C. Lee
Assistant Examiner—Fiona T. Powers
Attorney, Agent, or Firm—Roger N. Coe

[57] ABSTRACT

Newly synthesized chromogenic thiol-indicating benzoisothiazolone derivatives having the structure:

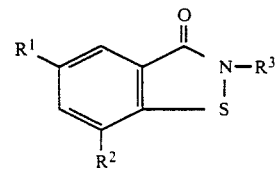

where $R^1$, $R^2$ and $R^3$ are as defined in the specification, are useful in the detection of thiols, particularly in an aqueous system. This process comprises contacting the aqueous system with a chromogenic thiol-indicating benzoisothiazolone derivative as described herein. Chromophoric changes due to thiol-mediated reduction of the benzothiazolone derivative then occur. Such changes can be in a solution or on an indicator surface in contact or having been in contact with the aqueous system. The chromophoric changes, due to a bathochromic shift in characteristic light absorption upon reduction of the benzoisothiazolone derivative, are proportional to the amount or rate of appearance of thiols in the aqueous system.

5 Claims, No Drawings

CHROMOGENIC THIOL INDICATORS BASED ON AN ISOBENZOTHIAZOLONE RING SYSTEM

RELATED APPLICATION

This application is a continuation of application Ser. No. 214,426, filed Jul. 1, 1988, now abandoned.

BACKGROUND OF THE INVENTION

The present invention relates to a new class of chromogenic thiol indicators based on the benzoisothiazolone (isobenzothiazolone) ring system. These indicators can be used in the detection of thiol groups produced by chemical or enzymatic reactions.

Classically, a number of color producing disulfides have been used for the detection of thiol residues. The most frequently used compound is the Ellman's reagent, 5,5'-dithio(2-nitrobenzoic acid), which in the presence of thiols produces the yellow color of p-nitrothiophenol at 405 nm (nanometers).

Other commonly used reagents for the detection of thiols include the 2,2'- and 4,4'-dipyridyl disulfides, whose reduced chromophore has an absorption at 340 nm.

There have been several attempts in the literature to prepare disulfide reagents which produce colors of longer wavelength and extinction. These compounds are of particular value in the development of diagnostic test systems because more highly colored substances can be more easily read in the presence of a number of colored interfering substances in urine, serum, and whole blood. None of these compounds (see the literature section) to date has found use in diagnostic application. This is largely because of a combination of factors, such as low reactivity with thiols due to their poor solubility or the poor chromogenic properties of the resulting reduced dyes in aqueous soluents.

1. Isobenzothiazolone Related Literature References a. Novel ring opening reaction of 2-aryl-1,2-benzoisoselenazol-3(2H)-one with thiols, N. Kamigata, M. Takata, H. Matsuyama, and M. Kobayashi, Heterocycles 24, 3027 (1986).

b. Antibacterial antimold treatment of photographic hydrophilic colloid for silver halide material by adding 1,2-benzoisothiazolin-3-one and isothiazolin-3-one derivatives, Konishiroku Photo Ind. Co., Ltd., Jpn. Kokai Tokyo Koho JP 55,142,543, Aug. 15, 1984.

c. Bacterial and fungicidal 1,2-benzoisothiazolin-3-one derivatives, Grivas. J. C. (Sherwin-Williams Co.), Ger. Offen. DE2119730, Nov. 11, 1971, Can. Pat. No. 914,682, Nov. 11, 1972.

d. 1,2-Benzoisothiazol-3-ones from dithiosalicylamides, T. Vitali, L. Amoretti, and V. Plazzi, Farmaco Ed. Sci. 23, 1075 (1968).

e. Preparation and antifungal activity of 1,2-benzoisothiazolin-3-ones with chlorine substitution in the benzene ring, R. Ponci, T. Vitali, F. Mossini, L. Amoretti, ibid. 22, 989 (1967).

f. N-Trichloromethylsulfenyl-1,2-benzoisothiazolones as fungicides and bacteriacides, R. Ponci, A. Baruffini, and P. Borgna, ibid. 21, 249 (1966). (Contains a preparation of 5-nitro derivative.)

g. 6-Nitro-1,2-benzoisothiazolones, R. Ponci, F. Gialdi, and A. Baruffini, ibid. 19, 254 (1964).

h. Antifungal activity of benzoisothiazolone and its derivatives, F. Gialdi, R. Ponci, and A. Baruffini, ibid. 19, 474 (1964).

i. Fungicidal properties of 5-nitro-1,2-benzoisothiazolones, R. Ponci, A. Baruffini, and F. Gialdi, ibid. 19, 121 (1964).

j. Preparation of 5-nitrobenzoisothiazolone and its derivatives, R. Ponci, A. Baruffini, M. Croci, and F. Gialdi, ibid. 18, 732 (1963).

k. On benzoisothiazolones: A series with a wide range of bacteriostatic and fungistatic activity, R. Fischer and H. Hurni, Arzneimittel-Forsch. 14, 1301 (1964). (N-acetyl derivatives and N-unsubstituted 5-nitro derivative.)

l. Bacteriostatic and fungistatic activity of benzoisothiazolones. Brit. Pat. No. 848,130, Mar. 14, 1958.

m. Effects of 1,2-benzoisothiazol-3-ones on platelet responsiveness to ADP and collagen, K. H. Baggaley, P. D. English, J. A. Jennings, B. Morgan, B. Nunn, and A. W. R. Tyrrell, J. Med. Chem. 28, 1661 (1985).

n. Methods of using spermicidal vaginal compositions comprising 1,2-benzoisothiazole derivatives, A. Butti and G. Gazzanni, U.S. Pat. No. 4,093,730 (1978). (Includes 5-nitro derivatives.)

o. Method for the production of 1,2-benzoisothiazol-3-ones, H. Hagen and H. Ziegler, (BASF AG), EP 0,082,398B1, Ger. Offen. DE 3,150,629, Jun. 30, 1983. (A process patent for the synthesis of unsubstituted derivatives.)

2. Isothiazolo Pyridinone References a. Isothiazolo pyridinones (to control phytopathogenic fungi), J. L. Rainey and M. C. Seidel, U.S. Pat. No. 3,965,107, Jul. 8, 1974.

b. Anti-acne composite containing as active ingredient a derivative of [5,5b]-isothiazolo pyridine-3-one, B. Shroot and J. Maignan, Fr. No. 2,555,450, May 31, 1985.

c. Synthesis and properties of some derivatives of [2H]-4,6-dimethylpyrido-[3,2b]isothiazolin-3-one, T. Zawisza and W. Malinka, Farmaco. Ed. Sci. 40, 124 (1985); ibid. 40, 133 (1985).

d. N-carbamoyl derivatives of [5,4b]-isothiazolo pyridine-3-one and anti-acne cosmetic compositions containing the same, U.S. Pat. No. 4,512,985, Apr. 23, 1985.

e. Anti-acne use of derivatives of [5,4b]isothiazolo pyridine-3-one, B. Shroot and J. Maignan, U.S. Pat. No. 4,548,942, Oct. 22, 1985.

3. Chromogenic Disulfide Related References a. Tissue sulfhydryl groups, G. Ellman, Arch. Biochem. Biophys. 82, 70 (1959). (Preparation and initial use of the Ellman's reagent.)

b. 2,2'-Substituted 4,4'-bis(4-pyridylazo-1-oxide)- diphenyl disulfides as reagents for photocolorimetric determination of thiols, K. V. Veksler, E. Yu Golubera, A. G. Goncharenko, A. N. LaVrent'ev, USSR SU 1,277,627 Al, Apr. 30, 1986; Chem. Abstr. 106: 43229f.

c. Reagent for colorimetric determination of hydrogen sulfide and thiols, K. V. Veksler and C. M. Trakhnova, USSR SU 1,085,937, Apr. 15, 1984; Chem. Abstr. 101: 103344y. [4-(arylazo)-phenyl disulfides.]

d. Method of obtaining a reagent for colorimetric determination of hydrogen sulfide on thiols; K. B. Veksler and G. M. Trakhnova, USSR SU 1,177,296A, Sep. 7, 1985. [Synthesis of 4,4'-bis-(1-hydroxy-8-chloro-3,6-disulfo-2-naphthylazo diphenyl disulfide).]

e. Aromatic disulfides in the detection of thiols, T. Novak, S. G. Pleva, and J. Epstein, Anal. Chem. 52, 1851 (1980). (Synthesis of Schiff base derivatives of 4,4'-dithiodianiline.)

f. Detection of thiols, T. Novak and M. T. Packard, U.S. patent application Ser. No. 301,507 AO, Mar. 26, 1982. (Synthesis of Schiff base derivatives of 4,4'-dithiodianiline.)

g. Test reagents for the detection of thiol groups and methods for their production, H. Heidenreich and K. Wehling, Bayer AG.

4. Miscellaneous Methods of Thiol Detection a. Japanese Pat. Appl. 59-106299, Jun. 19, 1984, A method for estimating NAD(P)H with oxidized glutathione in the presence of glutathione reductase and a color forming agent. Examples of color forming agents agents given are the Ellman's reagent, N-(1-anilinonaphthyl-4)maleimide, hydroxyethyl-2,4-dinitrophenyldisulfide, 2,2-dithiopyridine, and benzimidazoyl maleimide.

b. Japanese Pat. 57-135360, Aug. 20, 1982, Color indicator 4,4'-bisdimethylaminodiphenylcarbitol and a surfactant used in quantitation of the intensity of bad breath caused by thiol compounds. (Decolorization of a blue dye in the presence of thiols.)

c. A.-M. Seet and K.-T. Lee, Mikrochim. Acta 5-6, 577 (1975). Colorimetric method for the assay of lipoyl dehydrogenase, (Decolorization of a red 1,3-bis(2'-pyridyl)-1,2-diaza-prop-2-ene-Pd(II) complex by reduced lipoamide.)

d. L. -K. Tatt, I. -K. Tan and A. -M. Seet, Clinica. Chem. Acta 58, 101 (1975). A new colorimetric method for the determination of NADH/NADPH dependent glutathione reductase in erythrocytes and in plasma, (Decolorization of a red 1:1 chlorpromazine-Pd [II] complex by reduced glutathione.)

e. N. Aoyama, A. Miika, Y. Shimizu, and T. Tatano, Eur. Pat. Appl. EP 159,870 A2, Oct. 30, 1985. Determination of mercapto compounds and a reagent for this use. (Reaction of thiol with a peroxidase or thiol oxidase in the presence of a triarylmethane or triarylmethanol derivative to produce a colored pigment.)

The references in heading 1 are for the preparation and use of the isobenzothiazolone (benzoisothiazolone) class of compounds.

The title or a short description of the work is contained in each reference listing. Papers (b)–(o) describe the synthesis and use of these compounds in a variety of anti-infective purposes. Paper (a) by Kamigata and coworkers describes a reaction of the related benzoisoselenazolone analogs with thiols to give a non-chromogenic selenol product.

References under the heading 2 are for the synthesis and anti-bacterial properties of the pyridine analog of the invention (isothiazolopyridinones).

The references under heading 3 summarize a variety of chromogenic disulfide derivatives cited in the literature for the detection of thiols.

Finally, under heading 4, a number of thiol detection methods are summarized which do not exclusively utilize chromogenic disulfides.

The present invention is the first application of isobenzothiazolones and their derivatives for the chromogenic detection of thiol residues.

Advantages of compounds of the present invention over the classical disulfide derivatives cited under heading 4 include their smaller molecular size and geometry, and the ability to change their reactivity as indicators using the influence of various nitrogen side chains. The nitrogen side chain can also be used to immobilize the indicator to prevent interaction with other dyes.

SUMMARY OF THE INVENTION

The present invention involves a newly synthesized chromogenic thiol-indicating isobenzothiazolone derivative having the structure:

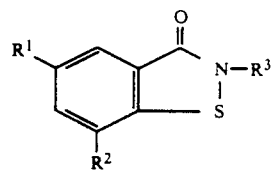

In this structure at least one of $R^1$ and $R^2$ is preferably nitro, arylazo, substituted arylazo, benzylideneamino or substituted benzylideneamino. When only one of $R^1$ and $R^2$ is so substituted, one of $R^1$ and $R^2$ may be hydrogen. The $R^3$ substituent is selected from alkyl groups having less than about 7 carbon atoms, amino, hydroxyl, alkoxyl, and aryl groups (and functionalized forms thereof) which provide the indicator with desired solubility and reactivity properties.

Preferred species of the isobenzothiazole derivative of the present invention comprise $R^1$ as nitro or arylazo and $R^2$ as hydrogen, for example Examples include compounds where $R^2$ is hydrogen and $R^1$ is phenylazo; substituted arylazo such as 4-hydroxyphenylazo; 4-nitro-2-methylphenylazo; 2-hydroxy-1-napthylazo; 2-hydroxy-5-methylphenylazo; 2-hydroxy-4-methyl-5-nitrophenylazo; 4-hydroxy-1-napthylazo; 4-hydroxy-3-methyl-1-napthylazo; 4-hydroxy-5-aza-1-napthylazo; 2-amino-1-napthylazo; 1-hydroxy-2-napthylazo; 3-N,N-dimethylaminopropylcarboxyamido-1-hydroxy-4-naphthylazo; 1-hydroxy-4-methoxy-2-naphthylazo; 2-hydroxy-3-carboxy-1-naphthylazo; 1-hydroxy-3, 6-disulfonato-2-naphthylazo; 2, 3-dihydroxy-1-naphthylazo; or 2-hydroxy-3, 5-dimethyl-1-phenylazo. In one particular embodiment $R^1$ is the substituted benzylideneamino, 2,4-dinitrobenzylideneamino and $R^2$ is hydrogen. Other indicators have $R^1$ as hydrogen and $R^2$ as 2-hydroxy-1-naphthylazo or 4-hydroxy-1-phthylazo or 4-hydroxy-1phenylazo.

In one aspect, particularly preferred compounds of the present invention, because of their utility in the detection of thiols in aqueous environments, have $R^3$ substituents with sufficient polarity to confer aqueous solubility upon the compound. For example, $R^3$ may be $—(CH_2)_nNR^4R^5$ where n is from 2 to 6 and $R^4$ and $R^5$ are simple alkyls or hydrogens. Other possible water solubilizing side chains include 3-carboxypropyl, sulfonatoethyl and polyethyl ethers of the type $—CH_2(CH_2OCH_2)_nCH_3$ where n is less than 10. For immobilization purposes, preferred compounds include $R^3$ side chains containing aminoalkyl, carboxyalkyl, omega amino polyethyl ethers and N-haloacetyl derivatives. In a broader sense, for various utilities $R^3$ may be alkyl, aryl, heteroaryl, alkoxy, hydroxy or amino groups. When including substitutions for solubility or reactivity purposes, $R^3$ may be aminoalkyl, carboxyalkyl, hydroxyalkyl or haloalkyl. The aryl or heteroaryl $R^3$ moieties may be substituted, for example as aminoaryl, carboxyaryl or hydroxyaryl.

A central utility of the compounds of the present invention involves their use in the detection of thiols. Thus, the present invention comprises a process for measuring the presence or appearance of thiols, particularly in an aqueous system. This process comprises contacting said aqueous system with a chromogenic thiol-indicating isobenzothiazolone derivative as described herein. Chromophoric changes due to thiol-mediated reduction of the isobenzothiazolone derivative then occur. Such changes can be in a solution or on an indicator surface in contact or having been in contact with the aqueous system. The chromophoric changes, due to a bathochromic shift in characteristic light absorption upon reduction of isobenzothiazolone derivative, are proportional to the amount or rate of appearance of thiols in the aqueous system.

The present invention may also be viewed as involving a chromogenic thiol-indicating isobenzothiazolone derivative having the structure:

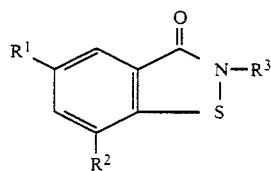

wherein at least one of $R^1$ and $R^2$ is nitro, arylazo, substituted arylazo, benzylideneamino or substituted benzylideneamino and one of $R^1$ and $R^2$ may be hydrogen and $R^3$ is a aminoallyl, aminoaryl and aminoheteroaryl, carboxyalkyl, carboxyaryl or carboxyheteroaryl covalently linked to a polymer comprising amino or hydroxy groups. The spacer arm $R^3$ can comprise oligmers of polyethylene-glycol and its derivatives. In one aspect, $R^3$ may be 17-chloracetamido-3,6,9,12,15-pentaoxyheptadecyl where hexaethylene glycol has been chloroacetamidated. When the polymer comprises hydroxyl groups, $Y^1$ and $R^3$ comprises carboxyl groups, the covalent linkage is preferably through an ester bond. When the polymer comprises amino groups, the analogous covalent linkage is through an amide bond. The amine-bearing polymer, when coupled to $R^3$, may be a polymer such as chitosan, polyalkylamine, aminodextran, polyethyleneimine, polylysine or aminostyrene.

The $R^3$ substituents of the present invention may also comprise an alkyl linked to an amine-bearing polymer by amine displacement of a halogen from an alpha-haloalkyl or alpha-haloalkylcarbox amido $R^3$ precursor. In the case of aminoalkyl or aminoaryl groups the $R^3$ substituent may also be covalently linked to a polymer such as polyepichlorohydrin, chloromethylpolystyrene, polyvinylalcohol or polyvinylpyridine. The $R^3$ substituent of the present invention may generally be an aminoalkyl, hydroxyalkyl, aminoaryl or hydroxyaryl group linked to a polymer comprising carboxyl groups through amide or ester linkages.

When polymers are involved in the $R^3$ structure, the polymer may be one such as polyacrylic acid, polymethacrylic acid, polyitaconic acid, oxidized polyethylene oxide, poly(methylmethacrylate/methacrylic acid), carboxymethyl cellulose, carboxymethyl agarose or carboxymethyl dextran. When such a carboxyl polymer is involved, the $R^3$ may be aminoalkyl (such as 6-aminohexyl, for example), hydroxyalkyl, aminoaryl or hydroxyaryl linked to the polymer through amide or ester linkages. In such cases, an $R^3$ precursor function may bear an amine or hydroxyl group to be covalently linked to a polymer by reaction with an acid anhydride-bearing polymer or by coupling with a carboxylate-bearing polymer through carbodiimide-induced bond formation.

The $R^3$ substituent or precursor thereto in the compound of the present invention may also be a haloalkyl or carboxyhaloalkyl moiety such as chloracetamido. Such a substituent may readily coupled to an amine-bearing polymer by amine displacement of the halogen.

DESCRIPTION OF PREFERRED EMBODIMENTS

"Aryl," as used herein, is intended to include organic residues derived from aromatic hydrocarbon or aromatic heterocyclic ring systems. Accordingly aryl groups include the unsubstituted ring residues such as phenyl and naphthyl and substituted forms thereof. Heterocyclic or heteroaryl residues may be those comprising one or more heteroatoms (e.g., nitrogen, oxygen, sulfur) in the ring system such as pyridyl, oxazolyl, quinolyl, thiazolyl and substituted forms thereof.

"Alkyl," as used herein, is intended to include aliphatic and cyclic organic residues having a carbon at a point of attachment. Accordingly, alkyl groups include unsubstituted hydrocarbon residues of the formula $C_nH_{2n+1}$ and substituted and cyclic forms thereof. Such hydrocarbons are usually of the lower alkyl class which have six carbons or less. It is understood that larger alkyl groups may be used but it is considered unlikely that these would have any benefit over the simpler compound. As stated above, alkyl includes substituted residues which are intended to include the hydrocarbon residues bearing one or more, same or different, functional groups as described below.

The alkyl and aryl group previously described may be substituted with functional groups. These groups are chosen such that they provide the necessary chromogenic or solubility properties which are desired in the final indicator. Such functional groups include essentially all chemical groups which can be introduced synthetically and result in stable compounds. Examples of these functional groups are hydroxyl, halo (fluoro, chloro, bromo), amino (including alkylamino and dialkylamino), cyano, nitro, carboxy (including carbalkoxy), carbamoyl (including N and N,N alkyl), sulfo, alkoxy, alkyl, aryl, and arylazo.

In general the chromogenic indicator compounds of the present invention have a characteristic UV-visible spectrum which changes after reaction with thiols and other reducing agents. In the preferred compounds this change results in a significant shift of the absorption maxima which can be detected either visually or instrumentally.

As mentioned earlier, these indicators are useful for detecting thiols such as, but not limited to, those produced by the reduction of disulfides. Specifically, these compounds are capable of detecting dihydrolipoamide (6,8-dimercaptooctamide) produced by the reaction of lipoamide dehydrogenase and NADH with lipoamide. Because NADH is generated by the oxidation of a substrate by a dehydrogenase, these compounds are capable of indirectly detecting such substrates. A typical NADH-generating system constitutes glucose dehydrogenase and its substrate, glucose.

The present invention will now be illustrated by description, preparation and application of these indicators.

These indicators of the present invention are of the general structure A:

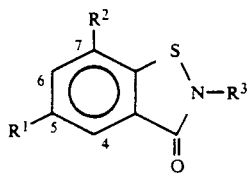

Where $R^1$ and $R^2$ are the same and are nitro, arylazo or arylideneamino or one is hydrogen and the other nitro, arylazo, or arylideneamino, and $R^3$ is chosen from a variety of alkyl, amino, hydroxy, alkoxyl, phenyl and aryl groups.

It is evident that the 4 and 6 positions on the ring can bear a variety of substituents without departing from the inventive features of these indicators. Such substituted forms shall be considered to be equivalents of the claimed indicators.

Compounds of Formula A where $R^1$ and $R^2$ are either hydrogen and/or nitro are prepared from the corresponding acid (Formula B).

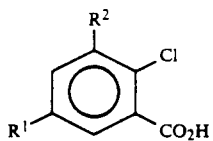

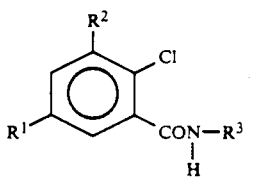

This acid can be converted to its acid chloride using thionyl chloride and then treated with an $R^3$ substituted amine to produce the amide of Formula C [Zabicky, *The Chemistry of Amides*, pp. 515–600, Interscience, New York, (1970)].

The chloride of Formula C is displaced with sulfide [Patai, *The Chemistry of the Thiol Group*, pt. 2, pp. 735–744, Wiley, New York (1974)]. Mild oxidation with $I_2$ produces the compound of Formula A.

Compounds of Formula A where $R^1$ and $R^2$ are arylideneamino, or one is hydrogen and the other arylideneamino, are prepared from the intermediate amide of Formula C. Treatment of this compound with an excess of sodium sulfide results in the displacement of the chloride and reduction of the nitro group to the amine. [H. K. Porter, *Org. Reactions*, Vol. 20, J. Wiley and Sons, New York, N.Y., pp. 455–481 (1973)]. Mild oxidation then furnishes the compound of Formula A where $R^1$ and $R^2$ are amino or one is amino and the other hydrogen.

These can be reacted with arylaldehydes with azeotropic removal of water to produce indicators of Formula A where $R^1$ and $R^2$ are Ar—C=N—, or one is ArC=N— and the other hydrogen.

Formula A where $R^1$ and $R^2$ are both arylazo, or one is arylazo and the other hydrogen, are prepared from the compound of Formula A where $R^1$ and $R^2$ are both amino or one is amino and the other hydrogen. There are two general methods which accomplish this. One is diazonium coupling [J. M. Tredder, *The Chemistry of Synthetic Dyes*, Vol. III, (K. Venkataramen, ed.) pp. 223–301, Academic Press, New York (1970); K. Venkataramen, *Synthetic Dyes*, Vol. I, pp. 409–649 (1952)] and the other the condensation of a nitroso compound with the amino [Boyer, *The Chemistry of the Nitro and Nitroso Groups*, Pt. 1 (Feuer, ed.), pp. 273–283, Intersciences, New York (1969)].

For the latter method, nitroso compounds must be prepared. The necessary compounds can be synthesized by oxidation of an aromatic amine [W. D. Langley, *Org. Synthesis*, Col. Vol. 3, p. 234, Wiley (1955)], or by reduction of an aromatic nitro Kubli, Chem. Ber. 41, 1936 (1908)] and then oxidation [E. Brill, Experentia, 835 (1974)]. Another preparation is the reaction of dimethylsulfonium chloride with an aromatic amine. The intermediate dimethyliminosulfurane is then oxidized to produce the nitroso compound. This method can be used to prepare either carbocyclic [A. D. Dawson and D. Swern, J. Org. Chem., 42, (4), 592 (1977)] or heterocyclic analogs [E. C. Taylor, C.-P. Tseng and J. B. Rampal, J. Org. Chem., 47, 552 (1982)].

The preferred indicators of Formula A are that of Formula D where $R^1$ is nitro or arylazo and $R^2$ is a water solubilizing group such as a sulfoalkyl carboxyalkyl, aminoalkyl (including N-alkyl and N,N-dialkyl) and polyethers of the type—$CH_2(CH_2OCH_2)_nCH_3$ where n is usually less than 4. Usually the alkyl groups are lower alkyl and linear of the type $(CH_2)_n$—X, where X is the functional group.

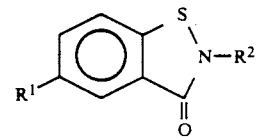

Especially preferred compounds are of Formula E where $R^1$ is nitro, 1-hydroxy-2-arylazo or 2-hydroxy-1-arylazo groups.

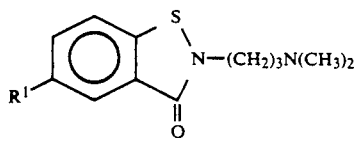

The preparation of several examples follows. These are intended to illustrate and not limit the present invention. In addition, the application of these indicators toward the detection of glucose is presented. This is intended to illustrate the utility of these indicators and not limit their application to these analytes.

EXAMPLE 1

3-N-(3-Dimethylaminopropyl)-5-nitroisobenzothiazol-3-one (IBTZ I)

The synthesis of N-(3-dimethylaminopropyl)-2-chloro-5-nitrobenzoamide was as follows. A suspension containing 20.1 g (grams) of 2-chloro-5-nitrobenzoic acid (0.1 mol), 6 mL (milliliters) of N,N-dimethylformamide (DMF), and 60 mL of thionyl chloride in 500 mL of $CH_2Cl_2$ was heated to reflux for 3 h (hours), during which a clear solution was obtained. The solvents were then evaporated in vacuo and the residual solid triturated once with hexane and dried under vacuum for 1 h. The solid was then placed under an inert atmosphere, dissolved in 500 mL of $CH_2Cl_2$, cooled to 0° C., and treated with a solution containing 10.21 g of 3-dimethylaminopropylamine in 200 mL of $CH_2Cl_2$ added dropwise over 2 h. The solution was then allowed to come to ambient temperature overnight. The resulting solution was then filtered and the filtrate then washed with brine and dried over $MgSO_4$. Filtration and removal of solvent gave 15.6 g of a light yellow solid, which was purified by flash chromatography on a 600 g column of $SiO_2$-60 (230-400 mesh) eluted with the following step gradients of $CHCl_3:CH_3OH:CH_3CO_2H$ solvent mixtures 110:10:1; 80:10:1; 50:10:1; 30:10:1. Fractions of 25 mL were taken. Fractions 95-540 were pooled and concentrated to give 17.2 g of yellow solid N-(3-dimethylaminopropyl)-2-chloro-5-nitrobenzoamide, which was recrystallized from ethyl acetate-hexane Yield 14.59 g (51%).

The analytical, nuclear magnetic resonance (NMR), infrared (IR) and mass spectral (MS) data of this compound were as follows:

Analysis calculated for $C_{12}H_{16}ClN_3O_3 \cdot H_2O$: C, 47.45; H, 5.97; N, 13.83. Found: C, 47.75; H, 5.98; N, 12.95.

$^1$H NMR (90 MHz, $CDCl_3$)δ: 2.05 (q, J=7 Hz, 2H); 2.50 (s, 6H); 2.88 (t, J=7 Hz, 2H); 3.58 (m, 2H); 7.56 (d, J=9 Hz, 1H); 8.20 (dd, J=9 Hz, 2 Hz, 1H); 8.42 (d, J=2 Hz, 1H); 10.3 (m, 1H).

IR (KBr): 3000, 1663, 1526, 1350 $cm^{-1}$.

Mass Spectrum (EI) m/e: 285.1 ($M^+$, 1.2%); 287.1 (M+2, 0.4%). (CI) m/e: 286.1 (M+1, 100%) 288.1 (m+3, 32.0%).

A solution containing 13.22 g of N-(3-dimethylaminopropyl)2-chloro-5-nitrobenzoamide (46.3 mmol) in 100 mL of $H_2O$ was added dropwise over a 45 minute period to a solution of 11.3 g of $Na_2S$ $9H_2O$ (47 mmol) in 100 mL of $H_2O$ maintained at 40° C. The resulting solution was then allowed to stir for 3 h at 40° C. The resulting thiol was treated with 20 mL of a $KI/I_2$ solution added dropwise over a 2 h period. Because no oxidation was noted, the solution was aerated, heated at 50° C., and treated with 60 mL of the $KI/I_2$ solution. The mixture was then heated overnight at 50° C. The precipitate was washed with ice water and dried overnight at 55° C., 0.1 mm pressure. The dried precipitate, 8.5 g, was found to contain partially purified product. This was dissolved in methanol, adsorbed on a small amount of $SiO_2$-60, and flash chromatographed on 500 g of $SiO_2$-60 (230-400 mesh) eluted with a 150:10:1 $CHCl_3$:MeOH:28% $NH_4OH$ solvent mixture with fractions of 25 mL taken. Fractions 112-270 contained the product and were pooled and concentrated to give 4.18 g of a light yellow product.

The supernatant solution from the reaction mixture was concentrated and flash chromatographed on 500 g $SiO_2$-60 using the same solvent system to obtain an additional 2.3 g of product. The combined product from the two columns was recrystallized from toluene-hexane to give 6.01 g of light yellow crystals (46% yield). mp 89.5°-90.5° C. The analytical, NMR, IR and MS data for this compound, (IBTZ I) were as follows:

Analysis: Calculated for $C_{12}H_{15}N_3O_3S$: 51.23; H, 5.37; N, 14.94. Found: C, 51.60; N, 5.50; N, 14.67.

$^1$H NMR (60 MHz, $CDCl_3$)δ: 2.0 (m, 2H); 2.25 (s, 6H), 2.35 (q, J=7 Hz, 2H); 4.05 (t, J=6 Hz; 2H); 7.73 (d, J=9 Hz, 1H); 8.47 (dd, J=9 Hz, 2 Hz, 1H); 8.88 (d, J=2 Hz, 1H).

IR (KBr): 3100, 2950, 2830, 2690, 1666, 1650, 1523, 1340 $cm^{-1}$.

The structure and certain optical properties of IBTZ I in solution are shown in Table 1.

EXAMPLE 2

5-Nitro-2-N-(3-N,N,N-trimethylammoniopropyl) isobenzothiazol-3-one iodide

A solution containing 0.5 g of IBTZ I (1.78 mmol) and 0.5 mL of iodomethane in 30 mL of $CH_2Cl_2$ was heated to reflux for 1 h. The product was then filtered, successively washed with $CH_2Cl_2$, ice water and acetone, and dried 4 h at 55° C. (0.1 mm). Yield 648 mg (86%). The analytical, NMR, IR data for this compound were as follows:

Analysis calculated for $C_{13}H_{18}IN_3O_3S$: C, 36.89; H, 4.29; N, 9.93. Found: C, 37.16; H, 4.25; N, 10.23.

$^1$H NMR (300 MHz, DMF-$d_7$)δ: 2.37 (m, 2H); 3.2 (s, H); 3.55 (m, 2H); 4.1 (t, J=6.7 Hz, 2H); 8.2 (d, J=9 Hz, 1H); 8.55 (dd, J=2.3 Hz, 8.8 Hz, 1H); 8.6 (d, J=2.1 Hz, 1H).

IR (KBr): 3030, 3010, 1660, 1600, 1518, 1340, 1040, 780 $cm^{-1}$.

EXAMPLE 3

N-(17-Amino-3,6,9,12,15-Pentaoxaheptadecyl)-5-Nitroisobenzothiazol-3-one (Amino-PEG IBTZ)

The title compound was prepared in steps (a) to (d) as described below.

(a) The synthesis of 1-Amino-17-(N-BOC-amido)-3,6,9,12,15-pentaoxaheptadecane was as follows. A solution of 5.76 g of t-butyl carbonate (26.4 mmol) in 30 mL of $CH_2Cl_2$ was added dropwise over 0.5 h to a stored solution containing 7.4 g of 1,17-diamino-3,6,9,12,15-pentaoxaheptadecane (prepared according to Kern et al. Makromol. Chem. 1979, 180 (10), 2539) in 50 mL of $CH_2Cl_2$. The resulting mixture was stirred for 0.5 h and then concentrated to an oil. The mixture was purified by flash chromatography on 600 g of $SiO_2$ eluted with 90:10:1 mixture of $CHCl_3:CH_3OH$:conc $NH_4OH$ and with 25 mL fractions taken. Fractions 135-201 contained the desired product and were pooled and concentrated to give 3.05 grams of an oil which was used without further purification. (30% yield)

The analytical, NMR, IR and MS data for this compound were as follows:

Analysis: calculated for $C_{17}H_{36}N_2O_7 \cdot \frac{1}{2}H_2O$: C, 52.42, H, 9.47, N, 7.19. Found C, 52.20; H, 8.84; N, 7.30.

$^1$H NMR (60MHz, $CDCl_3$)δ: 1.4 (s, 9H); 1.9 (m, 2H, $NH_2$); 2,8-3.1 (m, 3H); 3.3-3.6 (m, 6H); 3.67 (s, 16H).

IR ($CHCl_3$): 3010, 2930, 2875, 1706, 1509, 1248, 1101 $cm^{-1}$.

Mass Spectrum (EI) m/e: 381 (M+1, 2.7%) (CI) m/e: 381 (M+1, 100%)

(b) The synthesis of N-oxysuccinimidyl 2-chloro-5-nitrobenzoate was as follows. A solution of 21.67 g of N,N-dicyclohexylcarbodiimide (0.1 mol) in 140 mL of $CH_2Cl_2$ was added dropwise over 1 h to an ice cold stirred suspension containing 20.1 g of 2-chloro-5-nitrobenzoic acid (0.1 mol), 12.65 g of N-hydroxysuccinimide (0.11 mol), and 600 mL of $CH_2Cl_2$. The resulting mixture was stirred for 1 h at 0° C. and was then allowed to come to ambient temperature overnight. The mixture was then filtered and the precipitate washed twice was a small amount of $CH_2Cl_2$. The solvents were then removed in vacuo to give 32.94 g of a pink solid. Recrystallization of the N-oxysuccinimidyl 2-chloro-3-nitrobenzoate from toluene-hexane gave 28.3 g of off-white product in 95% yield, which was used without further purification, mp. 148°–151° C.

The analytical, NMR, IR and MS data for this compound were as follows:

Analysis: calculated for $C_{11}H_7ClN_2O_6$: 44.24; H, 2.36; N, 9.38. Found: C, 44.99; H, 2.84; N, 9.32

$^1$H NMR (60 MHz, $CDCl_3$)δ: 2.9 (s, 4H); 7.7 (d, J=9 Hz); 8.4 (dd, J=2 Hz, 9 Hz, 1H); 8.93 (d, J=2 Hz, 1H).

IR (KBr): 3000, 2990, 2930, 2850, 1810, 1780, 1740, 630 cm$^{-1}$.

MS (EI) m/e: 298 (M+, 0.4%); 300 (M+2, 0.2%); 114 (M-oxysuccinimidyl, 100%); 116 (36.9%).

(c) N-(17-BOC-Amido-3,6,9,12,15-pentaoxaheptadecyl)-2-chloro-5-nitrobenzoamide was prepared as follows:

A solution containing 3.04 g of 1-amino-17-(N-BOC-amido)-3,6,9,12,15-pentaoxaheptadecane (7.99 mmol) in 30 mL of $CH_2Cl_2$ was added dropwise over 0.5 h to an ice cold stirred solution containing 2.39 g of N-oxysuccinimidyl 2-chloro-5-nitrobenzoate (7.49 mmol) in 30 mL of $CH_2Cl_2$. The resulting mixture was allowed to stir for 0.5 h at 0° C. and 1 h at ambient temperature. The solution was then successively washed with water and brine, and was dried over $MgSO_4$. Filtration and removal of solvent gave 4.47 g of a yellow oil. The mixture was purified by flash chromatography on 500 g of $SiO_2$ eluted with a 49:1 $CHCl_3$—$CH_3OH$ solvent mixture, with 20 mL fractions taken. Fraction numbers 126–155 containing the product were pooled and concentrated to an oil. The oil was dissolved in $CHCl_3$, treated with activated charcoal and filtered through Celite, and concentrated to give 3.34 g of product as a yellow oil (70% yield).

The analytical, NMR, IR data for this compound were as follows:

Analysis: calculated for $C_{24}H_{38}ClN_3O_8$ 3/2$H_2O$: C, 51.56; H, 7.39; N, 7.52. Found: C, 51.78; H, 6.78; N, 7.58.

$^1$H NMR (60 MHz, $CDCl_3$)δ: 1.4 (s, 9H); 3.0–3.4 (m, 6H); 3.6–3.8 (m, 20H); 7.6 (d, J=9 Hz, 1H); 8.2 (dd, J=9 Hz, 2H, 1H); 8.4 (d, J=2H, 1H).

IR ($CHCl_3$): 3030, 2940, 1675, 1635, 1526, 1350, 1213, 1102, 668 cm$^{-1}$.

(d) 2-N-(17-Amino-3,6,9,12,15-pentaoxaheptadecyl)5-Nitroisobenzothiazolin-2-one Hydrochloride (Amino-PEG-IBTZ) was synthesized as follows.

A solution containing 600 mg of 2-N-(17-N-BOC-amido-3,6,9,12,15-pentaoxaheptadecyl)5-nitroisobenzothiazolone and 3 mL of 3N HCl was allowed to stir for 1 h at ambient temperature. Complete conversion of starting material (Rf=0.8) to product (Rf=0.3) was noted by analytical TLC ($SiO_2$, 90:10:1 $CHCl_3$-$CH_3OH$-conc. $NH_4OH$). The solvents were then removed in vacuo to given 570 mg of a yellow oil which was used without further purification.

The analytical, NMR, IR data for this compound were as follows:

Analysis calculated for $C_{19}H_{29}N_3O_8S·HCl·H_2O$: C, 44.40; H, 6.28; N, 8.18. Found: C, 44.21; H, 6.40; N, 7.72.

$^1$H NMR (60 MHz, $CDCl_3$)δ: 3.2 (m, 2H); 3.64 (m, 14H); 3.8 (m, 6H); 4.1 (m, 4H); 8.2 (d, J=8 Hz, 1H); 8.2 (m, 1H); 8.5 (dd, J=8 Hz, 2 Hz, 1H); 8.8 (d, J=2 Hz, 1H).

IR ($CHCl_3$): 2970, 2915, 1693, 1524, 1343, 1226, 1110 cm$^{-1}$.

EXAMPLE 4

N-(17-Chloracetamido-3,6,9,12,15-Pentaoxaheptadecyl)-5-Nitroisobenzothiazol-3-one (Chloroacetamido-PEG IBTZ).

A solution containing 50 mg of amino-PEG-IBTZ (0.1 mmol), 14 mL of triethylamine (0.1 mmol), and 17 mg of chloroacetic anhydride (0.1 mmol) in 0.5 mL of DMF were allowed to stir for 1 h at RT (room temperature). Partial conversion of starting material (Rf=0.5) was noted by TLC ($SiO_2$, 90:10:1 $CHCl_3$-$CH_3OH$-conc. $NH_4OH$). An additional 34 mg of chloroacetic anhydride and 28 mL of triethylamine was added and the resulting solution was stirred for 1 h at RT. The solvents were removed in vacuo with the residue taken up in 3 mL of ethyl acetate and filtered. The filtrate was then successively washed with 3 mL of 0.5N HCl and brine, and was dried ($MgSO_4$). Filtration and removal of solvent gave 30 mg of the product as a yellow oil (63% yield).

The IR and NMR data for this compound were as follows:

$^1$H NMR (300 MHz, $CDCl_3$)δ: 3.53 (q, J=5.5 Hz, 2H); 3.60 (t, J=4.9 Hz, 1H); 3.7 (m, 16H); 3.81 (t, J=4.7 Hz, 2H); 4.08 (s, 2H); 4.13 (s, 2H); 4.15 (m, 3H); 7.73 (d, J=8.9 Hz, 1H); 8.45 (dd, J=8.9 Hz 2.2 Hz, 1H); 8.88 (d, J=2.1 Hz, 1H).

IR ($CHCl_3$): 3000, 1736, 1669, 1515, 1344, 1210, 1120 cm$^{-1}$.

EXAMPLE 5

N-(3-Dimethylaminopropyl)-5,7-Dinitroisobenzothiazol-3-one (IBTZ II)

The synthesis of N-(3-dimethylaminopropyl)-2-chloro-3,5-dinitrobenzamide was as follows. A suspension of 2-chloro-3,5-dinitrobenzoic acid containing 25% water was dried by refluxing a suspension of the material in toluene with azeotropic removal of water. The solid, 12.33 g (0.05 mol), was suspended in 125 mL of $CH_2Cl_2$ containing 0.5 mL of DMF and 15 mL (0.20 mol) of thionyl chloride and then refluxed for 1 h. The solvents were removed in vacuo and the residue dissolved in 125 mL of $CH_2Cl_2$. While maintaining the reaction temperature at −20° C., 5.1 g (0.05 mol) of 3-dimethylaminopropylamine was added dropwise. After stirring for 5 min, the reaction mixture was filtered to yield 16 g (83%) of the hydrochloride salt. A portion (10.0 g) was dissolved in 100 mL of water and the pH adjusted to 12 using 1N NaOH solution. The mixture was extracted three times with 100 mL of EtOAc and the combined extracts washed once with 100 mL of water and then once with 100 mL of saturated NaCl solution. After drying ($Na_2SO_4$) the combined organic layers, the solvent was evaporated in vacuo to yield 7.0 g of the product as a dark red solid, mp 81°–84° C.

The analytical and NMR data for this compound were as follows:

Analysis: calculated for $C_{12}H_{15}O_5N_4Cl$: C, 43.46; H, 4.54; N, 16.95. Found C, 43.41; H, 4.68; N, 16.54.

$^1$H NMR (60 MHz, $CDCl_3$)δ: 8.48 (d, J=2, 1H); 8.41 (d, J=2, 1H); 3.3–3.8 (m, 1H), 2.50 (t, J=6, 2H); 2.30 (s, 6H); 1.5–2.0 (m, 2H).

A solution containing 1.65 g (5 mmol) of N-(3-dimethylaminopropyl)-2-chloro-3,5-dinitrobenzamide in 10 mL of anhydrous $CH_3OH$ was prepared and degassed with a stream of argon. The mixture was added to a similarly degassed solution of 0.38 g (5 mmol) of potassium hydrogen sulfide in 10 mL of MeOH. The reaction was stirred for 3 h and then $I_2$, 0.774 g (0.6 mmol), in 15 mL of $CH_3OH$ was added dropwise. After stirring for 16 h, the mixture was filtered and the solid dissolved in 10 mL of water. Once the aqueous solution was extracted twice with EtOAc and the pH was adjusted to 12, it was extracted three more times with 100 mL of EtOAc. These last three organic extracts were combined, dried ($Na_2SO_4$), filtered and then evaporated to yield 0.9 g of a yellow solid, mp 113°-115° C.

The analytical, NMR, IR and MS data for this compound (IBTZ II) were as follows:

Analysis: calculated for $C_{12}H_{14}N_4OS$: C, 44.1; H, 4.32; N, 17.1. Found: C, 43.41; H, 4.07;

$^1H$ NMR (300 MHz, $CDCl_3$)δ9.32 (d, J=2, 1H); 9.18 (d, J=2, 1H); 4.10 (t, J=7, 2H); 2.36 (t, J=7, 2H), 2.26 (s, 6H); 1.93-2.06 (tt, J=7, 2H).

IR (KBr): 1660, 1620, 1520, 1340 $cm^{-1}$.

Mass spectrum EI m/e: 326 (m+, 22.3%).

The structure and optical properties in solution of IBTZ II are shown in Table 1.

EXAMPLE 6

5-Nitroisobenzothiazol-3-one

Synthesis of 2-chloro-5-nitrobenzamide was as follows. A mixture of 40 g (0.198 mol) of 2-chloro-5-nitrobenzoic acid in 100 mL of thionyl chloride was refluxed for 1 h. The solvent was evaporated in vacuo to produce a red oil which was azeotroped several times with $CCl_4$. The crystalline acid chloride, thus obtained, was added in small portions over a 15 min (minutes) period to 200 mL of cold concentrated $NH_4OH$. Filtration after 15 min of additional stirring yielded 39.3 g (99%) of the 2-chloro-5-nitrobenzamide, mp 174°-175° C. (lit 178° C.).

The analytical data for this compound were as follows:

Analysis: calculated for $C_7H_5ClNO_3$: C, 41.91; H, 2.51; N, 13.97. Found: C, 41.39; H, 2.59; N, 13.92.

The synthesis of 5-nitroisobenzothiazol-3-one was as follows. A solution of 4.4 g (0.022 mol) of 2-chloro-5-nitrobenzamide in 75 mL of EtOH was heated to reflux and 50 mL of an aqueous solution containing 5.78 g (0.024 mol) of $Na_2S \cdot 9H_2O$ was added dropwise. Refluxing was continued for 1 h and then the reaction cooled to 50° C. A solution of 12 g of $I_2$ in 300 mL of 5% aqueous KI was added dropwise until the dark brown color of the mixture changed to a permanent pale yellow. The 5-nitroisobenzothiazol-3-one was collected by filtration to give 1.72 g (40%) of a yellow solid, mp 297°-298° C. (lit. 300° C. Farmaco Ed Sci, 1968, 23 1075-80).

The IR and MS data for this compound were as follows:

IR (KBr) 1664 $cm^{-1}$

Mass spectrum EI: 196 (M+).

EXAMPLE 7

N-(3-Dimethylaminopropyl)-5-Aminoisobenzothiazol-3-one (5-Amino IBTZ)

A mixture of 20.75 g (0.073 mol) of N-(3-dimethylaminopropyl)-2-chloro-5-nitrobenzamide, 57.0 g (0.238 mol) of $Na_2S \cdot H_2O$ and 100 mL of distilled water was refluxed, under Argon, for 1 h. Meanwhile a solution of 18.4 g (0.073 mol) of $I_2$ in 250 mL of $CH_3OH$ was prepared and then added dropwise to the $Na_2S$ reaction mixture which was cooled to room temperature. The $CH_3OH$ was removed in vacuo and the pH raised to 12 with 5% aqueous NaOH. The mixture was extracted twice with 250 mL of $CHCl_3$ and the combined extracts were dried ($Na_2SO_4$) filtered and concentrated. The residue was flash chromatographed on $SiO_2$-60 (230-400 mesh), eluting with a 60:10:1 (v/v/v) $CHCl_3$:MeOH:conc. $NH_4OH$ solution. Fractions 52-65 (20 mL/fraction) were pooled and concentrated to produce 6.4 g (35%) of a light yellow solid, mp 101°-103° C.

The analytical, NMR, IR and MS data for this compound were as follows:

Analysis: calculated for $C_{12}H_{17}N_3OS$: C, 57.34; H, 6.81; N, 16.71. Found: C, 56.59; H, 6.39; N, 16.26.

$^1H$ NMR (60 MHz, $CDCl_3$)δ7.13 (m, 2H); 6.83 (dd, J=2,8, 1H); 3.83 (t, J=7, 2H}; 2.33 (broad t, 2H); 2.17 (s, 6H); 1.83 (q, J=7, 2H).

IR (KBr); 3350, 3200, 1640 $cm^{-1}$.

Mass spectrum (EI) m/e: 251 (M+, 9%).

EXAMPLE 8

N-(3-Dimethylaminopropyl)-5-(4-Hydroxyphenylazo)Isobenzothiazol-3-one (IBTZ III)

The pH of a solution of 3.98 g (0.016 mol) of N-(3-dimethylaminopropyl)-5-aminoisobenzothiazol-3-one in 200 mL of water was adjusted to 2.0 using 2.5N aqueous HCl. After cooling to 5° C., a solution of 1.1 g (0.016 mol) of $NaNO_2$ in 20 mL of water was added dropwise and the reaction stirred for 30 min at 0°-5° C. A mixture of 1.5 g (0.016 mol) of phenol in 20 mL of $CH_3OH$ was added dropwise and the pH raised to 6.0 with 2N aqueous NaOH. After stirring overnight at room temperature, the pH was adjusted to 9.0 and the reaction extracted twice with 150 mL of $CHCl_3$. The extracts were combined, dried ($Na_2SO_4$), filtered and concentrated. Flash chromatography of the residue on 350 g of $SiO_2$-60 (230-600 mesh), eluting with a 60:10:1 (v/v/v) $CHCl_3$:$CH_3OH$:conc. $NH_4OH$ solvent system provided the product in fractions 48-80 (15 mL/fraction). They were pooled and concentrated to yield the product as an orange solid, 2.37 g (41%), mp 148°-151° C.

The analytical, NMR, IR and MS data for this compound (IBTZ III) were as follows:

Analysis: calculated for $C_{18}H_{20}N_4O_2S$: C, 60.65; H, 5.65; N, 15.72. Found: C, 60.60; H, 5.61; N, 15.58.

$^1H$ NMR (60 MHz, $CDCl_3$)δ: 8.47 (d, J=2, 1H), 8.17 (dd, J=2,8, 1H); 7.83 (d, J=9, 2H); 7.60 (d, J=8, 1H); 6.93 (d, J=9, 2H); 4.00 (broad t, J=7, 2H); 2.50 (broad t, 2H); 2.32 (s, 6H); 2.00 (broad q, 2H).

IR (KBr): 1650, 1590, 1140 $cm^{-1}$

Mass spectrum (EI) m/e: 356 (M+, 13.4%).

The structure and certain optical properties of IBTZ III in solution are shown in Table 1.

EXAMPLE 9

N-(3-Dimethylaminopropyl)-5-(4-Nitro-2-Methylphenylazo)isobenzothiazol-3-one (IBTZ IV)

A mixture of 0.12 g (0.72 mmol) of 4-nitro-2-methylnitrosobenzene (Langley, Org. Synth. Vol. III, Horing, ed., p. 334 (1955) and 0.18 g (0.71 mmol) of N-(3-Dimethylaminopropyl)-5-aminoisobenzthiazol-3-one was refluxed in 10 mL of 9:1 (v/v) $CH_3OH$ HOAc for 2 h, under argon. Another 0.2 g of the nitroso compound was added and the refluxing continued overnight. After cooling to room temperature, the reaction was filtered and the filtrate concentrated in vacuo. The residue was chromatographed on 95 g of SiO$_2$-60 (70-230 mesh), eluting with a 120:10:1 (v/v/v) CHCl$_3$:MeOH:conc. NH$_4$OH solution. Fraction numbers 24-33 (12 mL/fraction) were combined and evaporated to yield 0.12 g of the product as a red solid, softening at 111°-115° mp, 134°-135° C. The NMR, IR and mass spectral characteristics of this compound (IBTZ IV) were as follows:

$^1$H NMR (60 MHz, CDCl$_3$)δ: 8.50 (d, J=2, 1H); 8.23-7.90 (m, 3H); 7.78-7.53 (m, 2H); 3.98 (t, J=7, 2H); 2.80 (s, 3H); 2.37 (broad t, 2H); 2.22 (s, 6H); 2.00 (broad q, 2H).

IR (KBr): 1640, 1600, 1520, 1340, cm$^{-1}$.

Mass spectrum (EI) m/e: 399 (M+, 7.5%).

The structure and certain optical properties of IBTZ IV in solution are shown in Table 1.

EXAMPLE 10

N-(3-Dimethylaminopropyl)-5-(2,4-Dinitrobenzylideneamino)isobenzothiazol-3-one (IBTZ V)

A mixture of 0.9 g (4.59 mmol) of 2,4-dinitrobenzaldehyde (Aldrich Chemical Co.) and 1.15 g (4.58 mmol) of N-(3-Dimethylaminopropyl)-5-aminoisobenzothiazol-3-one in 60 mL of toluene was refluxed overnight with azeotropic removal of water. The solvent was removed in vacuo and the residue slurried in 50 mL of refluxing Et$_2$O. After the solid was filtered, it was dissolved in 50 mL of refluxing CH$_3$OH. The mixture was concentrated to a volume of 30 mL and the precipitate collected. The product, 0.66 g (32%), was obtained as an orange solid, mp 147°-149° C..

The analytical, NMR, IR and MS data for this compound (IBTZ V) were as follows:

Analysis: calculated for C$_{19}$H$_{19}$N$_5$O$_5$S: C, 53.14; H, 4.46: N, 16.31, Found: C, 52.65; H, 4.36; N, 16.33.

$^1$H NMR (60 MHz, CDCl$_3$)δ: 9.03 (s, 1H); 8.85 (m, 1H); 8.50 (s, 2H); 7.90 (broad s, 1H); 7.68 (d, 2H); 3.98 (t, J=7, 2H); 2.38 (broad t, 2H); 2.25 (s, 6H); 2.00 (broad q, 2H).

IR (KBr) 1640, 1600, 1525, 1340 cm$^{-1}$.

Mass spectrum (FAB) m/e: 440 (M++1, 4.0%).

The structure and certain optical properties of this compound (IBTZ V) in solution are shown in Table 1.

EXAMPLE 11

N-(3-Dimethylaminopropyl)-5-Phenylazoisobenzothiazol-3-one (IBTZ VI)

A mixture of 0.13 g (1.2 mmol) of nitrosobenzene (Aldrich Chemical Co.) and 0.3 g (1.2 mmol) of N-(3-dimethylaminopropyl)-5-aminoisobenzothiazol-3-one in 10 mL of 9:1 (v/v) CH$_3$OH: HOAc was refluxed overnight, under argon. An additional 50 mg of nitrosobenzene was added and the refluxing continued for 3 h. After the solvent was removed in vacuo, the residue was chromatographed on 65 g of SiO$_2$-60 (70-230 mesh), eluting with a 120:10:1 (v/v/v) CHCl$_3$:CH$_3$OH:conc. NH$_4$OH solution. Fractions 17-26 were combined and evaporated to yield 0.2 g (38%) of a yellow solid, mp 68°-71° C.

The analytical, NMR, IR and MS data for this compound (IBTZ VI) were as follows:

Analysis: calculated for C$_{18}$H$_{20}$N$_4$OS: C, 63.50; H, 5.92; N, 16.45. Found: C, 64.28; H, 5.98; N, 16.38.

$^1$H NMR (60 MHz, CDCl$_3$)δ: 8.30 (d, J=2, 1H); 8.13 (dd, J=2,8, 1H); 7.97-7.30 (m, 5H); 3.93 (t, J=7, 2H); 2.33 (broad t, 2H); 2.23 (s, 6H); 1.97 (broad q, J=7, 2H).

IR (KBr) 3430, 1635, 1595 cm$^{-1}$.

Mass spectrum (EI) m/e: 340 (M+, 7.1%)

The structure and certain optical properties of IBTZ VI in solution are shown in Table 1.

EXAMPLE 12

N-(3-Dimethylaminopropyl)-5-(2-Hydroxy-1-napthylazo)isobenzothiazol-3-one (IBTZ VII)

The same procedure described herein as used for IBTZ IX was followed on a 1.2 mmol scale. The residue was chromatographed on 100 g of SiO$_2$-60 (60-230 mesh), eluting with the solvent system 60:10:1 (v/v/v) CHCl$_3$:CH$_3$OH:conc. (concentrated) NH$_4$OH. A red solid, 0.23 g (47%) was isolated, mp 119°-124° C.

The analytical, NMR, IR and MS data for this compound were as follows:

Analysis: calculated for C$_{22}$H$_{22}$N$_4$O$_2$S: C, 65.00; H, 5.45; N, 13.78, Found: C, 65.46; H, 5.47; N, 13.53.

$^1$H NMR (60 MHz, CDCl$_3$)δ: 8.60 (m, 1H); 8.38 (d, J=2, 1H); 8.0-7.2 (m, 6H); 6.93 (d, J=9, 1H); 4.05 (broad t, 2H); 2.8-1.8 (broad, 10H).

IR (KBr): 1650, 1640, 1615, 1595, 1390, 1240 cm$^{-1}$.

Mass spectrum (EI) m/e: 406 (M+, 2.8%).

The structure and certain optical properties of IBTZ VII in solution are shown in Table 1.

EXAMPLE 13

N-3-(Dimethylaminopropyl)-5-(2-Hydroxy-5-methylphenylazo)isobenzothiazol-3-one (IBTZ VIII)

Except for the chromatography, the procedure used for IBTZ IX as described herein was followed. The chromatography was run using a solvent system of 60:10:1 (v/v/v) CHCl$_3$:CH$_3$OH:conc. NH$_4$OH. The product (0.23 g, 31%) was recovered as an orange solid, mp 123°-124° C.

The analytical, NMR, IR and MS data for this compound (IBTZ VIII) were as follows:

Analysis: calculated for C$_{19}$H$_{22}$N$_4$S: C, 61.60; H, 5.98; N, 15.12. Found: C, 60.76; H, 5.65; N, 14.59.

$^1$H NMR (60 MHz, CDCl$_3$)δ: 8.48 (d, J=2, 1H); 8.13 (dd, J=2,8, 1H);: 7.62 (m, 2H); 7.30-6.80 (m, 3H); 3.98 (t, J=7, 2H); 2.32 (s, 3H); 2.50-2.10 (broad s, 8H); 1.95 (broad q, 2H).

IR (KBr) 1640, 1600 cm$^{-1}$.

Mass spectrum (EI) m/e: 370 (M+, 4%).

The structure and certain optical properties of IBTZ VIII in solution are shown in Table 1.

EXAMPLE 14

N-(3-Dimethylaminopropyl)-5-(2-Hydroxy-4-nitro-5-methylphenylazo)isobenzothiazol-3-one (IBTZ IX)

Sodium nitrite (0.14 g, 2 mmol) was dissolved in a solution of 0.51 g (2 mmol) of N-(3-dimethylaminopropyl)-5-aminoisobenzothiazol-3-one in 40 mL of water. The mixture was cooled to 5° C. and 2.5N aqueous HCl added until pH 2.0 was obtained. After stirring for 20 min, 4-methyl-3-nitrophenol (0.306 g, 2 mmol) dissolved in 5 mL of CH$_3$OH was added dropwise. The reaction was allowed to warm to room temperature and stirred overnight. The pH was raised to 9 with 2N aqueous NaOH and the mixture extracted twice with 50 mL of CHCl$_3$. The combined extracts were dried (Na$_2$SO$_4$), filtered and concentrated in vacuo. Chromatography of the residue on 50 g of SiO$_2$-60 (60-230 mesh), eluting with a solvent composed of 120:10:1 (v/v/v) CHCl$_3$: CH$_3$OH:conc. NH$_4$OH, produced the product in fractions 13-20 (10 mL/fraction). These were combined and evaporated to yield 70 mg (9%) of a red solid, m.p. 177°–181° C.

The analytical, NMR, IR and MS data for this compound (IBTZ IX) were as follows:

Analysis: calculated for $C_{19}H_{22}N_4O_2S$: C, 61.60; H, 5.98; N, 15.12. Found: C, 60.76; H, 5.65; H, 14.59.

$^1$H NMR (60 MHz, CDCl$_3$)δ: 8.46 (d, J=7, 1H); 8.20 (m, 1H); 7.70 (d, J=8, 1H); 7.20 (m, 2H); 4.00 (t, J=7, 2H); 2.37 (s, 3H); 2.22 (broad, 10H).

IR (KBr) 1630, 1600, 1530 cm$^{-1}$.

Mass spectrum (EI): 415 (M+, 9.8%).

The structure and certain optical properties of IBTZ IX in solution are shown in Table 1.

EXAMPLE 15

N-(3-Dimethylaminopropyl)-5-(1-hydroxy-2-naphthylazo)isobenzothiazol-3-one (IBTZ XIV) and N-3(Dimethylaminopropyl)-5-(4-hydroxy-1-naphthylazo)isobenzol-3-one (IBTZ X)

A solution of 0.5 g (2 mmol) of N-(3-dimethylaminopropyl)-5-aminoisobenzothiazol-3-one in 50 mL of H$_2$O was prepared and cooled to 5° C. The pH was lowered to 2 and then a mixture of 0.14 g (2 mmol) of NaNO$_2$ in 2 mL of H$_2$O was added dropwise. Whenever the pH rose to 3, it was readjusted to 2 with 2.5N HCl. The reaction was allowed to stir for 20 min and then a solution of 0.28 g (2 mmol) of α-naphthol in 10 mL of CH$_3$OH was added. After stirring for 1 h, the pH was raised to 11.5 and the reaction extracted four times with 75 mL of CHCl$_3$. the combined organic extracts were dried (Na$_2$SO$_4$), filtered and concentrated. Chromatography of the residue on 100 g of SiO$_2$-60 (230–400 mesh) produced two products. The minor product eluted in fractions 15–23. These were combined and evaporated to yield 20 mg of a dark red solid, mp 115°–118° C.

Mass spectral datum for this compound was as follows:

Mass Spectrum (EI) m/e: 406 (M+, 17%).

Because α-naphthol is known to couple preferentially at the 4-position, the minor product was assigned the structure N-(3-dimethylaminopropyl)-5-(1-hydroxy-2-naphthylazo)isobenzothiazol-3-one (IBTZ XIV).

The major product, N-(3-dimethylaminopropyl)-5-(4-hydroxy-1-naphthylazo)-isobenzothiazol-3-one (IBTZ X), eluted in fractions 31–45 (15 mL fractions) to yield 0.32 g of a red solid which softened at 96°–100° C., resolidified, and then decomposed at 215°–220° C.

Mass spectral datum for this compound (IBTZ X) was as follows:

Mass spectrum EI (m/e): 406 (M+, 2.5%).

The structure and certain optical properties of IBTZ X and IBTZ XIV in solution are shown in Table 1.

EXAMPLE 16

N-(3-Dimethylaminopropyl)-5-(4-hydroxy-3-methyl-1-naphthylazo)isobenzothiazol-3-one (IBTZ XI)

A solution of 0.2 g (0.8 mmol) of N-(3-dimethylaminopropyl)-5-aminoisobenzothiazol-3-one in 30 mL of H$_2$O was prepared and then cooled to 5° C. The pH was lowered to 1.8 with 3N HCl then 0.54 g (0.8 mmol) of sodium nitrite, in 3 mL of H$_2$O, was added and the reaction allowed to stir for 20 min. A solution of 0.13 g (0.8 mmol) 2-methyl-1-naphthol in 5 mL of CH$_3$OH was then added dropwise. The reaction was allowed to warm to room temperature and stir overnight. After the pH was raised to 9.3, the mixture was extracted twice with 50 mL of CHCl$_3$. The pH of the aqueous phase was readjusted to 9 and the mixture extracted twice more with 50 mL of CHCl$_3$. The organic extracts were combined, dried (Na$_2$SO$_4$), filtered and the filtrate concentrated in vacuo. Chromatography of the residue on 100 g of SiO$_2$ (70–230 mesh), eluting with 120:10:1 (v/v/v) CHCl$_3$-CH$_3$OH-conc. NH$_4$OH, produced 0.13 g of a dark red solid, mp 94° C. The product eluted in fractions 17–24 (12 mL fractions).

The analytical, NMR, IR and MS data for this compound (IBTZ XI) were as follows:

Analysis: calculated for $C_{23}H_{29}N_4O_2S \cdot H_2O$: C, 62.99; H, 5.97; N, 12.77, Found: C, 62.80; H. 5.76; N, 12.53.

$^1$H NMR (300 mHz, CDCl$_3$), 8.38 (d, J=7.5, 1H), 8.17 (dd, J=7.5, 0.7, 1H), 8.12 (s, 1H), 7.91 (d, J=8.9, 1H), 7.85 (s, 1H), 7.57 (t, J=8, 1H), 7.45 (m, 2H), 2.88 (t, J=4.5, 2H), 2.25 (t, 2H), 2.10 (s, 6H), 1.82 (t, J=7, 2H).

IR (KBr); 3450, 3250, 1610, 1595, 1540, 1460 cm$^{-1}$.

Mass Spectrum EI (m/e, trimethysilylated): 492 (3.4%)

The structure and certain optical properties of IBTZ XI in solution are shown in Table 1.

EXAMPLE 17

N-(3-Dimethylaminopropyl)-5-(4-hydroxy-5-aza-1-naphthylazo)isobenzothiazol-3-one (IBTZ XII)

A solution of 0.5 g of (2 mmol) of N-(3-dimethylaminopropyl)-5-aminoisobenzothiazol-3-one in 50 mL of H$_2$O was prepared and its pH lowered to 2 with 2.5N HCl. After cooling to 5° C., a solution of 0.14 g (2 mmol) in 5 mL of H$_2$O was added dropwise. During the addition whenever the pH reached 3, it was lowered back to 2. The reaction was allowed to stir for 20 min and then a solution of 0.26 g (1.9 mmol) of 8-hydroxyquinoline in 5 mL of CH$_3$OH was added. The mixture was stirred for 30 min and then the pH raised to 7.1 with 3N NaOH.

Extraction with 50 mL of CHCl$_3$, followed by concentration of the aqueous layer, produced a residue which was chromatographed on 100 g of SiO$_2$ (70–230 mesh), eluting with 60:101 (v/v/v) CHCl$_3$:CH$_3$OH:- conc. NH$_4$OH. Fractions 11–19 (17 mL fractions) were combined and evaporated to yield 0.25 g of a dark maroon solid, mp. 173°–180° C.

The analytical, NMR, IR and MS data for this compound (IBTZ XII) were as follows:

Analysis: calculated for $C_{21}H_{21}N_5O_2S$: C, 61.89; H, 5.19; N, 17.18 Found: C, 61.26; H, 5.17, N, 16.47.

$^1$H NMR (60 MHz, D$_6$DMSO-CDCl$_3$, 4:1)δ: 9.30 (broad d, J=8, 1H), 9.00 (broad s, 1H), 8.32–7.80 (m, 5H), 7.25 (d, J=7, 1H), 3.97 (broad t, J=7, 2H), 2.40 (broad t, 2H), 2.22 (s, 6H), 1.90 (broad t, 2H).

IR (KBR): 1665, 1645, 1600, 1500, 1467, 1250, 1230 cm$^{-1}$.

Mass spectrum (EI) m/e: 407 (M+, 6.4%).

The structure and certain optical properties of IBTZ XII in solution are shown in Table 1.

EXAMPLE 18

N-(3-Dimethylaminopropyl-5-(2-amino-1-naphthylazo)isobenzothiazol-3-one (IBTZ XIII)

A solution of 0.5 g (2 mmol) of N-(3-dimethylaminopropyl)-5-aminoisobenzothiazol-3-one in 50 mL of H$_2$O) was prepared and its pH lowered to 2. After cooling to 5° C., 0.14 g (2 mmol) of NaNO$_2$ in 5 mL of H$_2$O was added dropwise. During the addition, whenever the pH rose to 3 it was readjusted back to 2. The mixture was allowed to stir for 20 min at 5° C. and then 0.29 g (2 mmol) of 2-aminonaphthalene in 5 mL of CH$_3$OH was added. The reaction was allowed to stir for 1 h and then the pH adjusted to 11 with 2.5N NaOH. After extracting twice with 50 mL of CHCl$_3$, the combined organic extracts were dried, filtered and the filtrate evaporated. The residue was chromatographed on 100 g of SiO$_2$ (70–230 mesh), eluting with 90:10:1 (v/v/v) CHCl$_3$:CH$_3$OH:conc. NH$_4$OH. The appropriate fractions were combined, and then concentrated to yield 0.42 g of a bright orange solid, mp. 175°–177° C.

The analytical, NMR, IR and MS data for this compound (IBTZ XIII) were as follows:

Analysis: calculated for C$_{23}$H$_{22}$N$_4$O$_4$S: C, 65.16; H, 5.72; N, 17.27, Found: C, 65.71; H, 5.94; N, 16.76.

$^1$H NMR (60 MHz, CDCl$_3$)δ: 8.93 (broad d, J=8, 1H), 8.53 (d, J=2, 1H), 8.20 (dd, J=2,8, 1H), 7.8–7.5 (m, 6H), 6.83 (d, J=9, 1H), 4.00 (t, J=7, 2H), 2.40 (broad t, 2H), 2.26 (s, 6H), 1 90 (broad t, 2H).

IR (KBr) 1660, 1630, 1560, 1510, 1440, 1343, 1265, 825 cm$^{-1}$.

Mass spectrum EI (m/e): 405 (M+, 22%).

The structure and certain optical properties of IBTZ XIII in solution are shown in Table 1.

EXAMPLE 19

Gantrez-N-6-aminohexylisobenzothiazol-3-one

The title compound was prepared as described in steps (a) and (b).

(a) N-(6-aminohexyl)-5-nitroisobenzothiazol-3-one hydrochloride was synthesized as follows. A solution of 2.2 g (10 mmol) of 2-chloro-5-nitrobenzoyl chloride in 25 mL of CH$_2$Cl$_2$ was added dropwise to a mixture of 6-t-butoxycarbonylamino-1-hexylamine hydrochloride (Stahl, et al. *J. Org. Chem.*, 43, 2285 (1978)). (2.5 g, 10 mmol) and triethylamine (2.0 g, 10 mmol) in 125 mL of CH$_2$Cl$_2$. After stirring overnight, 150 mL of H$_2$O and 100 mL of CHCl$_3$ were added. The organic phase was separated and the aqueous phase extracted three times with 100 mL of CHCl$_3$. The combined organic extracts were dried (Na$_2$SO$_4$), filtered and the filtrate concentrated to yield 3.5 g (88%) of N-(6-t-butoxycarbonylamino-1-hexyl)-5-nitrobenzamide as a white solid, mp 157°–159° C.

A slurry of 2.73 g (6.8 mmol) of this compound in 150 mL of CH$_3$OH was prepared and argon bubbled through for 10 min. While under argon, 0.59 g (8.2 mmol) of potassium hydrosulfide and 0.68 g (6.8 mmol) of triethylamine were added. The reaction was stirred overnight at room temperature and then 1.72 g (6.8 mmol) of I$_2$ in 75 mL of CH$_3$OH was added dropwise. Fifteen minutes after the completion of the addition, approximately 75 mL of CH$_3$OH was removed in vacuo. The mixture was diluted with 100 mL of CHCl$_3$ and 100 mL of H$_2$O. The aqueous phase was extracted twice more with CHCl$_3$, and the combined organic extracts were then dried (Na$_2$SO$_4$), filtered and concentrated. After the residue was dissolved in 30 mL of refluxing CH$_3$OH, it was cooled to room temperature and filtered The product, N-(6-t-butoxycarbonylaminohexyl)-5-nitroisobenzothiazol-3-one, crystallized when the filtrate was cooled to 3° C. Filtration produced 0.55 g (20%) of a yellow solid, mp 127°–130° C. This was added to 21 mL of 3N HCl in EtOAc and stirred for 20 min. Filtration produced 0.39 g of the title compound as a yellow solid, mp 211°–214° C. Analytical data for this compound were as follows:

Analysis: calculated for C$_{13}$H$_{18}$N$_3$O$_3$S.HCl: C, 47.06; H, 5.47; N, 12.66. Found: C, 46.96; H, 5.30; N, 12.61.

$^1$H NMR (60 mHz, D$_6$DMSO)δ: 8.42 (m, 3H), 8.05 (broad m, 3H, NH$_3$+), 3.90 (broad t, 2H), 2.80 (broad m, 2H), 2.0–1.2 (m, 8H).

IR (KBr): 3300, 1660, 1520, 1340 cm$^{-1}$.

(b) A solution of 1.0 g (3 mmol) of the above synthesized N-(6-aminohexyl)-5-nitroisobenzothiazol-3-one hydrochloride in 25 mL of DMF was prepared and 0.83 mL (5.9 mmol) of triethylamine added. This was added dropwise to a mixture of 0.89 g (6 mmol of anhydride) of Gantrez AN 119 (M.W. 20,000, GAF Corp.) in 15 mL of DMF. After stirring for 30 min, another 0.41 mL (3 mmol) of triethylamine in 45 mL of H$_2$O was added and the mixture stirred for 30 min.

Aqueous 1N HCl (5.9 mL) was added and a brownish solid precipitated immediately. The solvent was decanted and the solid stirred vigorously overnight in 100 mL of H$_2$O. The solid was collected and dried under high vacuum at 58° C. to yield 1.7 g of a pale yellow solid.

The analytical data for this compound were as follows:

Analysis: calculated for C$_{27}$H$_{35}$N$_3$O$_{12}$S: C, 51.83; H, 5.63; N, 6.71. Found: C, 49.88; H, 5.50; N, 7.58.

The structure and certain optical properties of Gantrez-N-6-aminohexylisobenzothizol-3-one in solution are shown in Table 1.

EXAMPLE 20

N-(3-Dimethylaminopropyl)-5-[1-hydroxy-2-(N-dimethylaminopropyl)carbamoyl-4-naphthylazo]isobenzothiazol-3-one (IBTZ XV)

A solution of 0.5 g (2 mmol) of 5-aminoisobenzothiazol-3-one in 50 mL of H$_2$O was prepared and its pH lowered to 1.8. After cooling to 5° C., a solution of 0.14 g (2 mmol) of NaNO$_2$ in 2 mL of H$_2$O was added dropwise. During the addition, the pH was readjusted to 1.8. After stirring for 20 min, 0.54 g (2 mmol) of 2-(N-dimethylaminopropylcarbamoyl)-naphthol in 5 mL of CH$_3$OH was added, with the pH maintained around 2. The reaction was allowed to stir for 30 min and then the pH was raised to 7. It was washed once with 50 mL of CHCl$_3$. The aqueous phase was separated and concentrated. Chromatography of the residue on 100 g of silica gel (70–230 mesh), eluting with 20:5:1 (v/v/v) CHCl$_3$:CH$_3$OH:conc. NH$_4$OH, produced the product in fractions 30–65 (17 mL fractions), mp 94°–97° C.

The following is the analytical and $^1$H NMR data. Anal. Calc'd for C$_{26}$H$_{34}$N$_6$O$_3$S: C, 61.15; H, 6.71; N, 16.45. Found: C, 61.45; H, 6.50; N. 15.39

$^1$H NMR (D$_6$DMSO, 60MHz)δ: 8.66 (s, 1H), 8.4–8.0 (m, 4H), 7.40 (broad t, 2H), 3.90 (broad t, 2H), 3.50 (broad m, 2H), 2.60 (s, 6H), 2.30 (s, 6H), 1.85 (m, 2H).

EXAMPLE 21

N-(3-Dimethylaminopropyl)-5-(4-methoxy-1-hydroxy-2-naphthylazo)isobenzothiazol-3-one (IBTZ XVI).

A solution of 0.5 g (2 mmol) of N-(3-dimethylaminopropyl)-5-aminoisobenzothiazol-3-one in 50 mL of water was prepared and the pH lowered to 2 with 3N HCl. After cooling to 5° C., a solution of 0.14 g (2 mmol) of NaNO$_2$ was added dropwise while maintaining the pH at 2. The reaction was allowed to stir for 20 min and then 0.34 g (2 mmol) of 4-methoxy-1-naphthol in 7 mL of CH$_3$OH was added dropwise. One hour later, 50 mL of EtOH was added and the pH raised to 6.5 with 3N NaOH. The solvent was removed in vacuo and the residue chromatographed on 150 g of silica gel (70–230 mesh) eluting with 120:10:1 (v/v/v) $CHCl_3$:$CH_3OH$:conc. $NH_4OH$. Fractions 24–33 (15 mL fractions) contained a red compound whose TLC spot turned blue when sprayed with mercaptoethanol. These fractions were combined and concentrated to yield 0.24 g of a red glass. Diethyl ether (10 mL) was added and the mixture filtered to produce a red solid, mp 115°–117° C.

The $^1H$ NMR, IR and MS data for this compound were as follows:

$^1H$ NMR (60 MHz, $CDCl_3$) 8.20–7.20 (m, 7H), 6.30 (s, 1H), 3.92 (s, 3H), 3.92 (g, 2H), 2.8–1 8 (m, broad s, 10H).

IR (KBr): 3455, 1655, 1509, 1482, 1191 $cm^{-1}$.

Mass spectrum (m/e=436 ($M^+$, 3.1%).

EXAMPLE 22

N-(3-Dimethylaminopropyl)-5-(3-carboxy-2-hydroxy-1-naphthylazo)isobenzothiazol-3-one (IBTZ XVII).

The diazonium salt of 5-amino IBTZ was prepared by the method described for IBTZ XV. A solution of 0.37 gm (2 mmol) of 3-hydroxy-2-naphthoic acid in 5 mL of $CH_3OH$ was then added dropwise. After stirring for 1 h at 5° C., the reaction was warmed to room temperature and its pH raised to 7. The solvent was evaporated and the residue chromatographed on silica gel (70–230 mesh), eluting with 7:3 (v/v) EtOH: 1 m aqueous 1M triethylammonium bicarbonate. Fractions 90–125 (15 mL fractions) were combined and evaporated to yield 0.29 g of a dark red solid, mp 235° C. The elemental analysis indicated the product was contaminated with an inorganic salt.

The analytical and $^1H$ NMR data for this compound were as follows:

Anal. Calc'd. for $C_{23}H_{21}N_4O_4SNa$: C, 58.46; H, 4.48; N, 11.86. Found: C, 48.97; H, 4.47; N, 9.47.

$^1H$ NMR ($D_6DMSO$, 300 MHz) : 8.85 (d, J=8.5, 1H), 8.51 (s, 1H), 8.24–8.13 (m, 3H), 7.89 (d, J=8, 1H), 7.56 (t, J=8, 1H), 7.31 (t, J=7.5, 1H), 3.91 (t, J=6.5, 2H), 2.48 (t, J=6.5, 2H), 2.29 (s, 6H), 1.89 (quint, 2H).

EXAMPLE 23

N-(3-Dimethylaminopropyl)-5-(1-hydroxy-3,6-disulfo-2-naphthylazo)isobenzothiazol-3-one (IBTZ XVIII) and IBTZ XIX The diazonium salt of 5-amino IBTZ was prepared as described for IBTZ XV in 40 mL of $H_2O$ on a 1 g scale of the amine. A solution of 0.28 g (4 mmol) of $NaNO_2$ in 10 mL of $H_2O$ was added dropwise. After stirring for 30 min, a solution of 0.69 g (4 mmol) of 1-naphthol-3,6-disulfonic acid (technical grade, Pfaltz and Bauer) in 20 mL of $H_2O$ was added to the reaction. The mixture was stirred for 1 h and the pH raised to 9. Isopropanol was then added and the mixture filtered The solid was slurried in 25 mL of 7:3 (v/v) EtOH: 1M aqueous triethylammonium bicarbonate. The soluble portion was flash chromatographed on 200 g of silica gel (230–400 mesh), eluting with the same solvent. Two spots were seen on TLC. The faster moving, major product was isolated by evaporating fraction 60–95 (17 mL fractions). This was assigned the structure of the title compound, IBTZ XVIII.

The minor component eluted in fractions 105–130. It remains unidentified but was assigned the sample designation of IBTZ XIX.

The analytical and $^1H$ NMR data on IBTZ XVIII were as follows:

Anal. Calc'd. for $C_{22}H_{20}N_4O_8S_2Na_2.2H_2O$: C, 40.86; H, 3.74; N, 8.66. Found: C, 41.20; H, 3.89; N, 7.86.

$^1H$ NMR ($D_6DMSO$, 300 MHz)δ: 8.23 (m, 3H), 8.09 (dd, J=9, 0.5, 1H), 7.89 (d, J=1, 1H), 7.73 (dd, J=8, 1.5, 1H), 7.57 (s, 1H), 3.87 (t, J=6.5, 2H), 2.25 (s, 6H), 1.88 (s, 1H), 1.85 (quint, 2H).

EXAMPLE 24

N-(3-Dimethylaminopropyl)-5-(2,3-dihydroxy-1-naphthylazo)isobenzothiazol-3-one (IBTZ XX)

The diazonium salt of 5-amino IBTZ was prepared as described for IBTZ XV on a 0.3 g scale of the amine in 15 mL of $H_2O$. A solution of 0.2 g (1.2 mmol) of 2,3-dihydroxynaphthalene in 5 mL of $CH_3OH$ was added dropwise. After stirring for 5 min, the pH was adjusted to 7 and the reaction allowed to stir at room temperature for 2 h. The solvent was removed and the residue chromatographed on 100 g of silica gel (70–230 mesh), eluting with 60:10:1 (v/v/v) $CHCl_3$:$CH_3OH$:conc. $NH_4OH$. Fractions 22–30 (15 mL fractions) were Combined and evaporated to yield 0.2 g of a dark red solid, mp 181°–185° C.

The analytical, $^1H$ NMR and IR data for this compound (IBTZ XX) were as follows:

Anal. Calc'd. for $C_{22}H_{22}N_4O_3S$: C, 62.54; H, 5.25; N, 13.26. Found: C, 62.68; H, 5.14; N, 12.59.

$^1H$ NMR (300 MHz, $D_6DMSO$)δ: 8.32 (broad d, J=8.9, 1H), 8.14 (m, 2H), 7.51 (broad dd, J=0.9, 7.7, 1H), 7.36 (d quint, J=1.6, 7.2, 2H), 7.12 (s, 1H), 3.85 (t, J=7.5, 2H), 2.28 (t, J=7.5, 2H), 2.17 (s, 6H), 1.82 (quint, J=7.5, 2H).

EXAMPLE 25

N-[3-Dimethylaminopropyl]-5-[2-hydroxy-3,5-dimethyl-1-phenylazo]isobenzothiazol-3-one (IBTZ XXI)

The diazonium salt of 5-amino IBTZ was prepared as described previously on 0.3 gm (1.2 mmol) scale of 5-aminoisobenzothiazol-3-one in 10 mL of $H_2O$. A solution of 0.08 g (1.2 mmol) of $NaNO_2$ in 1 mL of water as added dropwise to the cold (5° C.) reaction, while maintaining the pH at 2. To this was added a solution of 2,4-dimethylphenol in 5 mL of $CH_3OH$. The pH was raised to 7 and the mixture allowed to stir at room temperature for 1 h. The solvent was evaporated and the residue chromatographed on 100 g of silica gel (70–230 mesh), eluting with 120:10:1 (v/v/v) $CHCl_3$:$CH_3OH$:conc. $NH_4OH$. Fractions 21–27 (10 mL fractions) were combined and evaporated to yield 0.23 g of an orange solid, mp 153°–155° C.

The analytical $^1H$ NMR, mass spec. and IR data were as follows:

Anal. Calc'd. for $C_{20}H_{24}N_4O_2S$: C, 62.47; H, 6.29; N, 14.57. Found: C, 61.74; H, 5.95; N, 14.21.

$^1H$ NMR ($D_6DMSO$, 300 MHz)δ11.23 (s, 1H), 8.44 (d, J=1.8, 1H), 8.44 (dd, J=1.9, 8.7, 1H), 8.15 (d, J=8.7, 1H), 7.47 (d, J=1.4, 1H), 7.17 (d, J=1.1, 1H), 3.92 (t, J=7.5, 1H), 2.30 (s, 3H), 2.22 (s, 3H), 2.18 (s, 6H), 1.82 (quint, J=7.5, 2H).

EXAMPLE 26

N-(3-Dimethylaminopropyl)-7-aminoisobenzothiazol-3-one.

N-(3-Dimethylaminopropyl)-2-chloro-3-nitrobenzamide was prepared by the same procedure described for N-(3-dimethylaminopropyl)-2-chloro-5-nitrobenzamide in Example 1 and then a solution of 9.0 g (31.5 mmol) in $CH_3OH$ was added dropwise to a mixture of 32.0 g (133 mmol) of $Na_2S$ $9H_2O$ in 300 mL of $H_2O$. The reaction was refluxed for 1 h and then cooled in an ice bath. A solution of 17.0 g (67.5 mmol) of $I_2$ in $CH_3OH$ was added dropwise. After stirring for 2 h, the solid was filtered and the mother liquor extracted four times with $CHCl_3$. The $CH_3OH$ was evaporated away from the aqueous phase and then extracted twice more with $CHCl_3$. The combined organic extracts were dried ($Na_2SO_4$), filtered and concentrated. The residue was chromatographed on 200 g of silica gel (70-230 mesh) eluting with 90:10:1 (v/v/v) $CHCl_3/CH_3OH$/conc. $NH_4OH$. A pale yellow solid was isolated, 1.4 g, mp 122°-125° C.

The NMR, MS and IR data for this compound are as follows:

$^1H$ NMR (60 MHz, $CDCl_3$)δ: 7.48 (dd, J=1,8, 1H), 7.20 (dd, J=8,8, 1H), 6.86 (dd, J=1,8, 1H), 3.92 (t, J=8, 2H), 2.32 (t, 2H), 2.20 (s, 3H), 1.96 (broad t, 2H).

IR (KBr) 3374, 1630, 1585, 1486 $cm^{-1}$.

Mass spectrum EI m/e=251 ($M^+$ 12.4%).

EXAMPLE 27

N-(3-Dimethylaminopropyl)-7-(4-hydroxy-1-phenylazo)isobenzothiazol-3-one (IBTZ XXII).

A solution of N-(3-dimethylaminopropyl)-7-aminoisobenzothiazol-3-one (0.5 g, 2 mmol) in 50 mL of water was prepared and its pH lowered to 1.5 with 3N HCl. After cooling to 5° C., a mixture 0.14 g (2 mmol) of $NaNO_2$ in 2 mL of $H_2O$ was added dropwise. The reaction was allowed to stir for 20 min and then 0.18 g (2 mmol) of phenol in $CH_3OH$ was added. After adjusting the pH to 7, the reaction was allowed to stir for 2 h. The solvent was evaporated and the residue chromatographed twice.

The first chromatography was on 120 g of silica gel (70-230 mesh) eluting with 60:10:1 (v/v/v) $CHCl_3/CH_3OH$/conc. $NH_4OH$. The second on 50 g of silica gel, eluting with the same solvent. A total of 0.25 g of an orange solid was isolated, mp 194°-198° C.

The following is the analytical, NMR, IR and MS data for this compound:

Anal. Calc'd. for $C_{18}H_{20}N_4O_2$: C, 60.65; H, 5.65; N, 15.72. Found: C, 59.45; H, 5.57; N, 14.98.

$^1H$ NMR (300 MHz, $D_6DMSO$), 8.43 (dd, J=1, 7.5, 1H), 8.02 (dd, J=1, 7.5, 1H), 7.95 (d, J=9, 2H), 7.70 (dd, J=7.5, 7.5, 1H), 6.98 (d, J=9, 2H), 3.77 (t, J=7, 2H), 2.26 (t, J=7, 2H), 2.16 (s, 6H), 1.81 (q, J=7, 2H).

Mass spectrum EI (m/e)=356 ($M^+$, 20%), 228 ($M^+$-128, 100%).

EXAMPLE 28

3-(N-Dimethylaminopropyl)-7-(2-hydroxy-1-naphthylazo)isobenzothiazol-3-one (IBTZ XXIII)

A solution of 0.5 g (2 mmol) of 7-aminoisobenzothiazol-3-one in 50 mL of water was prepared and its pH lowered to 1.5. It was cooled to 5° C. and then a solution of 0.14 g (2 mmol) of NaNO in 10 mL of water was added dropwise. After 1 h, 0.288 g (2 mmol) of 2-naphthol, in 5mL of $CH_3OH$ was added dropwise. Twenty minutes later, the pH was raised to 7 and the mixture allowed to stir for 1 h. The solvent was evaporated and the residue chromatographed on 200 g of silica gel, eluting with 100:10:1 (v/v/v), $CHCl_3/CH_3OH$/conc. $NH_4OH$. The compound was isolated as a dark red solid, 200 mg, mp 161°-165° C.

The analytical, $^1H$ NMR and mass spec. data were as follows:

Anal. Calc'd. for $C_{22}H_{22}N_4O_2S$: C, 65.00; H, 5.45; N, 13.78. Found: C, 65.47; H, 5.64; N, 12.14.

$^1H$ NMR ($D_6DMSO$, 300 MHz)δ8.92 (d, J=8.5, 1H), 8.57 (d, J=7.6, 1H), 8.05 (d, J=7.9, 2H), 7.96 (d, J=8.1, 1H), 7.53 (t, J=7.4, 1H), 7.58 (d, J=7.9, 1H), 3.90 (t, J=6.5, 1H), 2.35 (t, J=6.7, 2H), 2.10 (s, 3H), 1.89 (quint J=6.6 2H).

Mass spectrum EI (m/e): 406 ($M^+$, 5.5%)

EXAMPLE 29

5-Nitro-2-(3-carboxypropyl)-isobenzothiazol-3-one

A mixture of 2.23 g (10 mmol) of 2-chloro-5-nitrobenzoyl chloride, 1.67 g (10 mmol) of ethyl-4-aminobutyrate hydrochloride and 25 mL of pyridine were stirred together at 5° C. for 4 h. The mixture was diluted with $CHCl_3$, washed twice with water, once with 3% HCl and once with saturated $NaHCO_3$ solution. The organic layer was separated, dried ($Na_2SO_4$), filtered and then concentrated to produce 1.67 g (53%) of a white solid, mp 76°-78° C.

Argon was bubbled through a solution of 3.5 mL (25.4 mmol) of triethylamine, 50 mL of $CH_3OH$ and 7.86 g (27.3 mmol) of the chloride and then 1.8 g (25 mmol) of KSH added. After stirring for 5 h, additional KSH (0.35 g) was added. Thirty minutes later, a solution of 6.1 g of $I_2$ in 100 mL of $CH_3OH$ was added dropwise During the addition, the color of the reaction would change from orange to colorless. Whenever this occurred, an additional 0.25 mL of triethylamine was added. The reaction was then filtered and then concentrated to a volume of about 50 mL. Filtration produced additional solid which was combined with the first and recrystallized from 150 mL of $CH_3OH$ to yield 4.45 g, mp 140°-142° C. of yellow solid, 5-nitro-2-(3-carbethoxypropyl)isobenzothiazol-3-one.

A mixture of 10 mL of formic acid and 25 uL of $H_2SO_4$ containing 0.25 the 5-nitro-2-(3-carbethoxypropyl)isobenzothiazol-3-one was heated in a 130° oil bath overnight. The reaction was cooled and then poured into 30 mL of water. After standing overnight, the mixture was filtered to yield 0.11 g of the title compound as a yellow solid, mp 183°-186° C.

The $^1H$ NMR, mass spec. and IR data are as follows:

The $^1H$ NMR (60 MHz $D_6DMSO$):δ8.20-8.40 (m, 3H); 3.90 (t, J=7.5, 2H); 2.60-1.80 (m, 4H).

IR(KBr): 3600-2100, 1730, 1690, 1620, 1510, 1440, 1340 $cm^{-1}$.

Mass spectrum (EI) m/e: 282 ($M^+$, 25.6%).

EXAMPLE 30

N-(N,N-Dimethylamino)-5-nitroisobenzothiazol-3-one

A mixture of 2-chloro-5-nitrobenzoic acid (10.4 g, 50 mmol) and 20 mL thionyl chloride was refluxed for 3 h. The solvent was removed in vacuo and 40 mL of toluene were added. The mixture was concentrated and 50 mL of hexane added. Filtration produced 9 5 g of the acid chloride, mp 56°-58° C.

This was dissolved in 50 mL of $CH_2Cl_2$ and added, dropwise to a cold solution of 5.1 g (86 mmol) of 1,1-dimethylhydrazine in 100 mL of $CH_2Cl_2$. The mixture was stirred in the cold for 45 min and then diluted with 100 mL of water and 300 mL of $CHCl_3$. The organic layer was separated, dried ($MgSO_4$), and then filtered.

Removal of the solvent, followed by recrystallization from isopropanol produced 7.5 g of N,N-dimethyl-2-chloro-5-nitrobenzohydrazide.

A solution of 6.5 g (27.3 mmol) of the above compund, 3.5 mL (25.4 mmol) of triethylamine in 50 mL of methanol was prepared. To this was added 6.0 g (2.75 mmol) of NaSH·9H$_2$O and the mixture allowed to stir for 18 h at room temperature under Argon. A solution of 6.1 g (2.4 mmol) of I$_2$ in 100 mL of methanol was then added dropwise. After stirring for 3 h the mixture was filtered. The filtrate was concentrated to a volume of 50 mL and the mixture filtered again. The two solids were combined, slurried in methanol, and the mixture heated to reflux. After filtering the hot solution, water was added to the filtrate until it became turbid and it was then allowed to cool. Filtration produced 1.5 g of the title compound as pale yellow solid, mp. 163°–169° C.

Anal. calcd. for C$_9$H$_9$N$_3$O$_3$S: C, 45.18; H, 3.79; N, 17.56, Found: C, 44.30; H, 3.55; N, 17.08.

EXAMPLE 31

Procedure for Determining UV-visible Spectrum of Reduced IBTZ Derivatives of the Present Invention A 50 umol/L (micromoles per liter) solution of each IBTZ derivative was prepared in 0.1M, pH 6.5 phosphate buffer and its UV-visible spectrum measured. [λmax $(ox)$] To 2.8 mL (0.14 umol) of these solutions were added 0.2 mL of a 160 umol/L (0.32 umol) of dithiothreitol (DTT) solution in the same buffer. The UV-visible spectrum of the reduced isobenzthiazolone was measured immediately unless otherwise noted. [λ]max$(red)$] These data are summarized in Table 1 for many compounds of the present invention.

TABLE 1

| | R$^1$ | R$^2$ | λ$_{max}$(ox) | λ$_{max}$(red) |
|---|---|---|---|---|
| IBTZ I | NO$_2$ 5-nitro | H | 342 | 404 |
| IBTZ II | NO$_2$ 5-nitro | NO$_2$ 7-nitro | 343 | 400 |
| IBTZ III | 5-(4-hydroxyphenylazo) HO—⟨⟩—N=N— | H | 369 | 408 |
| IBTZ IV | 5-(4-nitro-2-methylphenylazo) O$_2$N—⟨⟩—N=N— with CH$_3$ | H | 383 | 432 |
| IBTZ V | 5-(2,4-dinitrobenzylideneamino) O$_2$N—⟨⟩—C=N— with NO$_2$ | H | 381 | 448 |
| IBTZ VI | 5-phenylazo ⟨⟩—N=N— | H | 355 | 406 |
| IBTZ VII | 5-(2-hydroxy-1-naphthylazo) naphthyl-OH with N=N— | H | 490 | 510 |

TABLE 1-continued

Structure: R¹ and R² substituted benzene with C(=O)N(CH₂)₃N(CH₃)₂ and S groups

| | R¹ | R² | λ_max(ox) | λ_max(red) |
|---|---|---|---|---|
| IBTZ VIII | 5-(2-hydroxy-5-methylphenylazo) | H | 371 | 456 |
| IBTZ IX | 5-(2-hydroxy-4-methyl-5-nitrophenylazo) | H | 398 | 476 |
| IBTZ X | 5-(4-hydroxy-1-naphthylazo) | H | 470 | 484 |
| IBTZ XI | 5-(4-hydroxy-3-methyl-1-naphthylazo) | H | 460 | 512 |
| IBTZ XII | 5-(4-hydroxy-5-aza-1-naphthylazo) | H | 410, 472(sh) | 454 |
| IBTZ XIII | 5-(2-amino-1-naphthylazo) | H | 478 | 490 |

TABLE 1-continued

Structure: R¹ and R² substituted benzene with -C(=O)-N(CH₂)₃N(CH₃)₂ and -S- forming a thiazine-type ring.

| | R¹ | R² | $\lambda_{max}$(ox) | $\lambda_{max}$(red) |
|---|---|---|---|---|
| IBTZ XIV | 5-(1-hydroxy-2-naphthylazo) | H | 486 | 544 |
| XV | 5-[1-hydroxy-2-(N-dimethyl-aminopropylcarbamoyl)-4-naphthylazo] | H | 488 | 500 |
| XVI | 5-(1-hydroxy-4-methoxy-2-naphthylazo) | H | 508 | 562 |
| XVII | 5-(2-hydroxy-3-carboxy-1-naphthylazo) | H | 496 | 510 |
| XVIII | 5-(1-hydroxy-3,6-disulfo-2-naphthylazo) | H | 490 | 550 |
| XIX | Unidentified, see IBTZ XVIII preparation. | H | 498 | 554 |

TABLE 1-continued

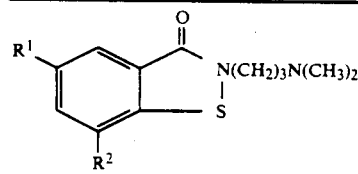

| | R¹ | R² | λ_max(ox) | λ_max(red) |
|---|---|---|---|---|
| XX | 5-(2,3-dihydroxy-1-naphthylazo) | H | 470 | 514 |
| XXI | 5-(2-hydroxy-3,5-dimethyl-1-phenylazo) | H | 370 | 456 |
| XXII | H | 7-(4-hydroxyphenylazo) | 428, 358 | 347[3] |
| XXIII | H | 7-(2-hydroxy-1-naphthylazo) | 472 | 540[3] |
| | Gantrez-N-6-aminohexyl-5-nitro-isobenzothiazol-3-one | | 343 | 412 |

[3] Read after 8 min.

Glucose Test

The ingredients in the film formula were added to 0.5 mL of water containing 0.5 g of Pipes buffer. The mixture was melted at 40°–45° under vacuum and then coated on polyethylene terephthalate.

Film Formula 5.0 g Bone Gel (pH = 6.8)   20 mg Lipoamide   Mixed with 0.5

-continued

| | | |
|---|---|---|
| 0.5 g Water | 400 μL LADH | grams water |
| 0.5 g Ethylene Glycol | 60 mg GDH | and 0.5 g Pipes. |
| 1.0 g PVP (20%) | 60 mg NAD | Add to vacuum |
| 0.5 g Olin 10 G (4%) | 40 mg BSA | flask when gel |
| 2.5 g Pipes Buffer (pH = 7) | 10 mg Diaphorase | melts and IBTZ |
| 0.04 g IBTZ | | is dissolved. |

Cast at 94.5 μ (Mayer Rod #42)

Crosslink Solution 7.5 g Water
2.5 g Olin 10 G (4%)
0.62 g Carbodimide
  Cast at 20.25 μ (Mayer Rod #9)

Testing Procedure

Ten strips were reacted with different levels of aqueous glucose standards (0, 20, 40, 70, 110, 140, 180, 250, 400, 800 mg/dL). The strips were allowed to react for 40 seconds and were then wiped dry. After wiping, the strips were untouched for ten minutes for the colors to stabilize before reading them on the Macbeth.

Abbreviations

PVP: polyvinylpyridine
10-G: Olin 10-G
Pipes: 1,4-piperazinebis(ethanesulfonic acid)
LADH: lipoamide dehydrogenase
GDH: glucose dehydrogenase
NAD: nicotinamide adenine dinucleotide
BSA: bovine serum albumin The a*, and b*, are coordinates which quantitate color. A* represents the green-red axis, and b* the blue-yellow. On the a* axis an intense red color is represented by the number +100 and an intense green color by −100. Similarly, on the b* axis, an intense blue is represented by a −100 and yellow by +100.

The term, delta E, is a number which quantitates the total color change from that at the next lower concentration. A delta E value of 5 can be is easily distinguished by the eye. These numbers are not standardized and can only be used to determine the relative color for a given indicator.

| IBTZ I | | | |
|---|---|---|---|
| a* | b* | Level (mg/dl) | delta E |
| −4.43 | 16.65 | 0 | — |
| −5.23 | 32.47 | 40 | 15.85 |
| −6.55 | 47.71 | 110 | 15.30 |
| −6.03 | 75.69 | 250 | 28.03 |
| −5.20 | 79.56 | 800 | 3.96 |

| IBTZ III | | | |
|---|---|---|---|
| a* | b* | Level (mg/dl) | delta E |
| −9.05 | 70.42 | 0 | — |
| −8.99 | 60.05 | 20 | 10.38 |
| −9.19 | 62.20 | 40 | 2.18 |
| −7.77 | 73.73 | 70 | 11.66 |
| −2.53 | 91.53 | 110 | 18.65 |
| 0.68 | 100.08 | 140 | 9.21 |
| 1.00 | 100.14 | 180 | 0.37 |
| −0.04 | 100.49 | 250 | 1.13 |
| 3.06 | 103.72 | 400 | 4.62 |
| 0.15 | 97.73 | 800 | 6.78 |

| IBTZ VII | | | |
|---|---|---|---|
| a* | b* | Level (mg/dl) | delta E |
| 32.25 | 58.20 | 0 | — |
| 36.40 | 52.79 | 20 | 9.86 |
| 40.90 | 46.63 | 40 | 10.20 |

| IBTZ VII -continued | | | |
|---|---|---|---|
| a* | b* | Level (mg/dl) | delta E |
| 33.83 | 30.69 | 70 | 18.04 |
| 35.71 | 24.81 | 110 | 14.99 |
| 22.39 | 5.09 | 140 | 24.50 |
| 21.72 | 1.24 | 180 | 4.15 |
| 14.80 | −2.24 | 250 | 10.20 |
| 19.35 | −2.63 | 400 | 5.22 |
| 20.19 | −0.54 | 800 | 2.49 |

| IBTZ VIII | | | |
|---|---|---|---|
| a* | b* | Level (mg/dl) | delta E |
| −6.93 | 88.15 | 0 | — |
| −7.66 | 85.06 | 20 | 3.19 |
| −7.43 | 81.55 | 40 | 3.54 |
| 4.25 | 85.89 | 70 | 13.53 |
| 15.97 | 90.05 | 110 | 13.76 |
| 23.25 | 87.35 | 140 | 8.53 |
| 26.83 | 88.15 | 180 | 4.59 |
| 31.89 | 81.09 | 250 | 9.28 |
| 34.07 | 78.86 | 400 | 3.24 |
| 33.79 | 78.39 | 800 | 0.57 |

| IBTZ IX | | | |
|---|---|---|---|
| a* | b* | Level (mg/dl) | delta E |
| −5.68 | 50.57 | 0 | — |
| −4.99 | 59.78 | 20 | 9.40 |
| −1.99 | 63.53 | 40 | 5.39 |
| 21.45 | 41.45 | 70 | 35.58 |
| 27.31 | 36.36 | 110 | 9.01 |
| 31.76 | 33.82 | 140 | 6.27 |
| 35.45 | 20.72 | 180 | 14.49 |
| 34.65 | 27.48 | 250 | 7.09 |
| 38.06 | 14.64 | 400 | 14.51 |
| 38.06 | 15.61 | 800 | 1.06 |

Many variations may be made in the compounds and derivatives of the present invention without departing from the scope and spirit of the following claims.

What is claimed is:

1. A chromogenic thiol-indicting benzoisothiazolone derivative having the structure:

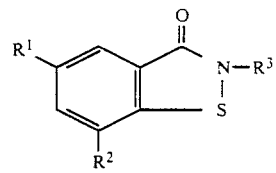

wherein at least one of $R^1$ and $R^2$ is benzylideneamino; or 2,4-dinitrobenzylideneamino; $R^1$ or $R^2$ or neither is hydrogen; and $R^3$ is alkyl; carboxyalkyl; hydroxyalkyl; aminoalkyl; haloalkyl; aryl; carboxyaryl; hydroxyaryl; aminoaryl; a heterocyclic radical selected from the group consisting of pyridyl, oxazolyl, quinolyl and thiazolyl which is unsubstituted or substituted by carboxy, hydroxy or amino; hydroxyl; alkoxy; or amino.

2. The isobenzothiazole derivative of claim 1 wherein $R^1$ is benzylideneamino.

3. The isobenzothiazole derivative of claim 1 wherein $R^2$ is benzylideneamino.

4. The isobenzothiazole derivative of claim 1 wherein $R^1$ is 2,4-dinitrobenzylideneamino.

5. The isobenzothiazole derivative of claim 1 wherein $R^2$ is 2,4-dinitrobenzylideneamino.

* * * * *